(12) United States Patent
Chow et al.

(10) Patent No.: US 11,844,902 B2
(45) Date of Patent: Dec. 19, 2023

(54) GAS WASHOUT VENT FOR PATIENT INTERFACE

(71) Applicant: ResMed Pty Ltd, Bella Vista (AU)

(72) Inventors: Tatt Hoong Chow, Singapore (SG); Muditha Pradeep Dantanarayana, Sydney (AU); Rahul Khera, Sydney (AU); Dimitri Marco Maurer, Gosford (AU); Min Li Tee, Singapore (SG)

(73) Assignee: ResMed Pty Ltd, Bella Vista (AU)

( * ) Notice: Subject to any disclaimer, the term of this patent is extended or adjusted under 35 U.S.C. 154(b) by 94 days.

(21) Appl. No.: 17/508,067

(22) Filed: Oct. 22, 2021

(65) Prior Publication Data

US 2022/0040431 A1 Feb. 10, 2022

Related U.S. Application Data

(63) Continuation of application No. 16/348,895, filed as application No. PCT/AU2017/051231 on Nov. 9, 2017, now Pat. No. 11,160,944.

(Continued)

(51) Int. Cl.
*A61M 16/00* (2006.01)
*A61M 16/06* (2006.01)
(Continued)

(52) U.S. Cl.
CPC ....... *A61M 16/0622* (2014.02); *A61B 5/4818* (2013.01); *A61M 16/06* (2013.01);
(Continued)

(58) Field of Classification Search
CPC .......... A61M 16/0622; A61M 16/0627; A61M 16/0633; A61M 16/0866; A61M 16/06;
(Continued)

(56) References Cited

U.S. PATENT DOCUMENTS

| 4,612,926 A | 9/1986 | Boiarski |
| 4,782,832 A | 11/1988 | Trimble et al. |

(Continued)

FOREIGN PATENT DOCUMENTS

| EP | 2 027 880 A1 | 2/2009 |
| JP | 2002-95751 A | 4/2002 |

(Continued)

OTHER PUBLICATIONS

International Search Report for PCT/AU2017/051231, dated Jan. 30, 2018, 7 pages.

(Continued)

*Primary Examiner* — Steven O Douglas
(74) *Attorney, Agent, or Firm* — Nixon & Vanderhye P.C.

(57) ABSTRACT

A gas-washout vent includes a housing with a first wall with one or more passages through the wall configured to provide fluid communication with a portion of the patient interface system exposed to a therapy pressure. The passages include respective first openings on a first surface of the first wall. The housing at least partially defines a second opening in communication with ambient atmosphere. A diffusing material is located at least partially within the housing to be adjacent the first surface. A surface of the diffusing material facing the first surface is spaced away from the first surface by a gap that extends to provide a fluid communication between all of the first openings and between all of the first openings and the second opening. The housing is configured so that air is prevented from flowing out of the housing at all areas directly opposite each of the first openings.

11 Claims, 24 Drawing Sheets

Related U.S. Application Data

(60) Provisional application No. 62/420,678, filed on Nov. 11, 2016.

(51) Int. Cl.
*A61B 5/00* (2006.01)
*A61M 16/08* (2006.01)
*A61M 16/16* (2006.01)
*A61M 16/20* (2006.01)
*A61M 16/12* (2006.01)

(52) U.S. Cl.
CPC .... *A61M 16/0627* (2014.02); *A61M 16/0633* (2014.02); *A61M 16/0683* (2013.01); *A61M 16/0866* (2014.02); *A61M 16/009* (2013.01); *A61M 16/0066* (2013.01); *A61M 16/0875* (2013.01); *A61M 16/125* (2014.02); *A61M 16/16* (2013.01); *A61M 16/20* (2013.01); *A61M 2205/42* (2013.01); *A61M 2230/42* (2013.01)

(58) Field of Classification Search
CPC ............ A61M 16/0683; A61M 16/125; A61M 16/0066; A61M 16/009; A61M 16/0875; A61M 16/16; A61M 16/20; A61M 2205/42; A61M 2230/42; A61B 5/4818
See application file for complete search history.

(56) References Cited

U.S. PATENT DOCUMENTS

| | | |
|---|---|---|
| 4,944,310 A | 7/1990 | Sullivan |
| 6,532,959 B1 | 3/2003 | Berthon-Jones |
| 6,581,594 B1 | 6/2003 | Drew et al. |
| 7,866,944 B2 | 1/2011 | Kenyon et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 10,695,527 B2 | 6/2020 | Dantanarayana |
| 2001/0003327 A1 | 6/2001 | Sanders |
| 2006/0266365 A1 | 11/2006 | Stallard |
| 2009/0044808 A1 | 2/2009 | Guney et al. |
| 2009/0044810 A1 | 2/2009 | Kwok et al. |
| 2009/0050156 A1 | 2/2009 | Ng et al. |
| 2010/0000534 A1 | 1/2010 | Kooij et al. |
| 2010/0083969 A1 | 4/2010 | Crumblin |
| 2011/0180071 A1 | 7/2011 | Veliss |
| 2012/0132209 A1 | 5/2012 | Rummery |
| 2012/0304985 A1 | 12/2012 | Lalonde |
| 2014/0283831 A1 | 9/2014 | Foote |
| 2014/0366882 A1 | 12/2014 | Ng et al. |
| 2015/0209541 A1 | 7/2015 | Harwood |
| 2016/0008558 A1 | 1/2016 | Huddart et al. |
| 2016/0263409 A1 | 9/2016 | Lee |
| 2016/0310687 A1 | 10/2016 | McAuley et al. |
| 2019/0262568 A1 | 8/2019 | Chow et al. |

FOREIGN PATENT DOCUMENTS

| | | | |
|---|---|---|---|
| JP | | 2009-50707 A | 3/2009 |
| JP | | 2013-540032 A | 10/2013 |
| JP | | 2014-526319 A | 10/2014 |
| JP | | 2014-208306 A | 11/2014 |
| JP | | 2017-527365 A | 9/2017 |
| WO | | 98/004310 A1 | 2/1998 |
| WO | | 98/034665 A1 | 8/1998 |
| WO | | 2000/078381 A1 | 12/2000 |
| WO | | 2004/073778 A1 | 9/2004 |
| WO | | 2005/063328 A1 | 7/2005 |
| WO | | 2006/074513 A1 | 7/2006 |
| WO | | 2006/130903 A1 | 12/2006 |
| WO | WO | 2007/012140 A1 | 2/2007 |
| WO | | 2009/052560 A1 | 4/2009 |
| WO | | 2010/135785 A1 | 12/2010 |
| WO | | 2012/171072 A1 | 12/2012 |
| WO | | 2013/020167 A1 | 2/2013 |
| WO | WO | 2014/129913 A1 | 8/2014 |
| WO | | 2016/041019 A1 | 3/2016 |
| WO | | 2016/119018 A1 | 8/2016 |

OTHER PUBLICATIONS

International Preliminary Report on Patentability with Amended Sheets, completed Mar. 1, 2019, 139 pages.
Written Opinion of the International Preliminary Examining Authority ISA for PCT/AU2017/051231, dated Jan. 11, 2019, 4 pages.
Written Opinion of the International Preliminary Examining Authority ISA for PCT/AU2017/051231, dated Jul. 19, 2018, 6 pages.
Written Opinion of the International Preliminary Examining Authority ISA for PCT/AU2017/051231, dated Oct. 17, 2018, 5 pages.
Written Opinion of the ISA for PCT/AU2017/051231, dated Jan. 30, 2018, 7 pages.
"*Respiratory Physiology*", by John B. West, Lippincott Williams & Wilkins, 9$^{th}$ edition published 2012 (8 pages).
Extended European Search Report dated May 27, 2020 in European Application No. 17870371.6, 6 pages.
Chow et al., U.S. Appl. No. 16/348,895, filed May 10, 2019 for "Gas Washout Vent for Patient Interface," (parent application).

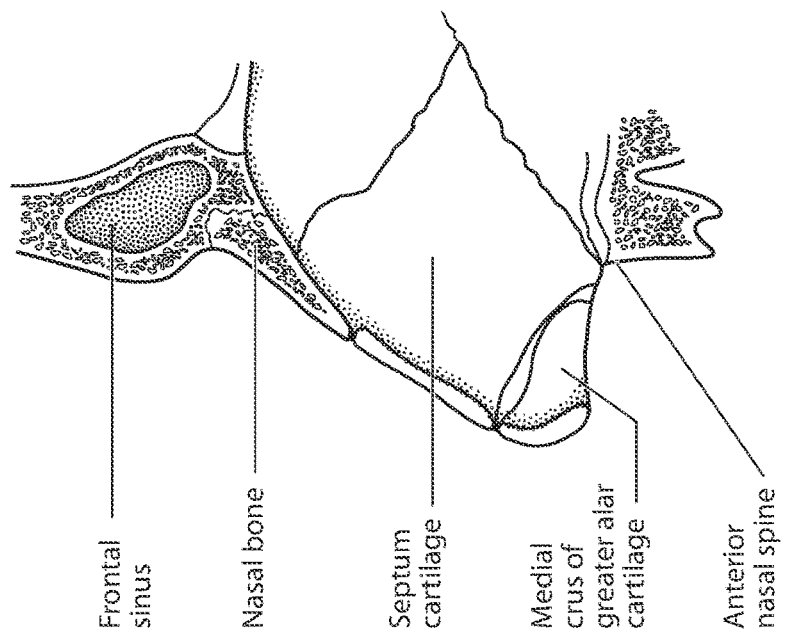
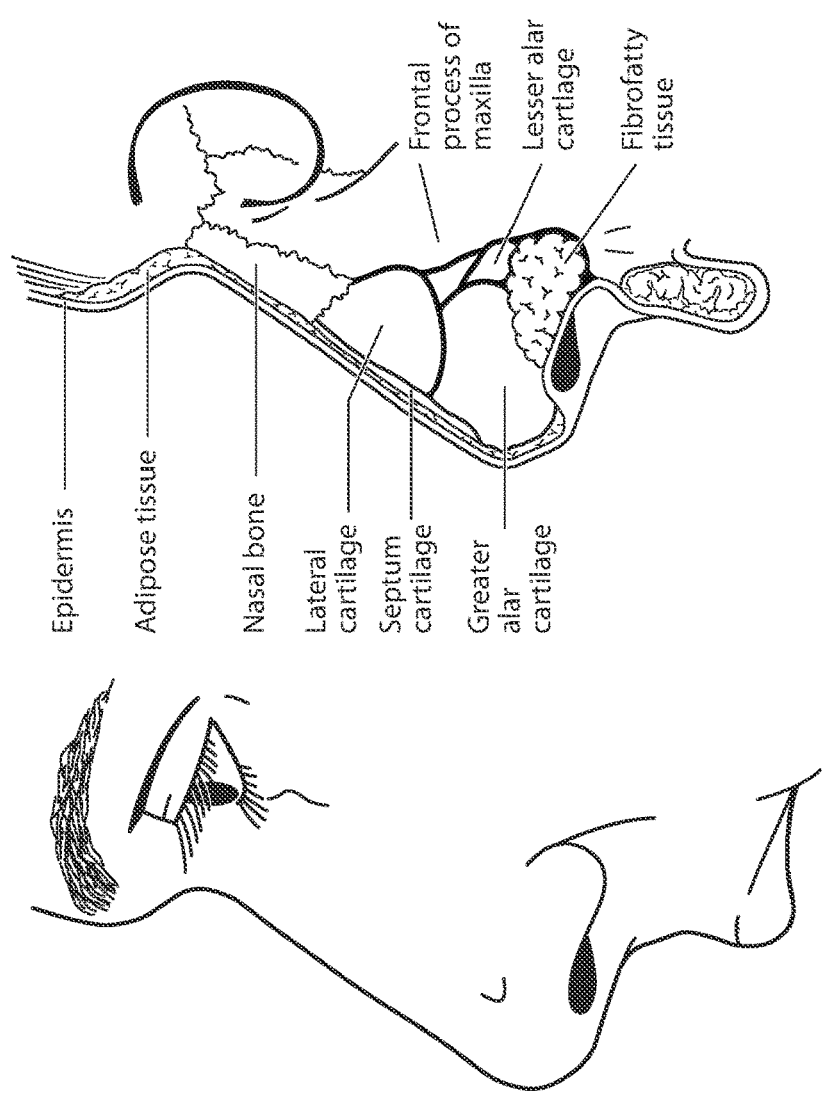
FIG. 2G  FIG. 2H  FIG. 2I

Relatively Large Positive Curvature

Relatively Small Positive Curvature

Zero Curvature

Relatively Small Negative Curvature

Relatively Large Negative Curvature

Copyright 2015 ResMed Limited

Left-hand rule

Right-hand rule

Left ear helix

Right-hand helix
Right-hand positive

Right ear helix

Copyright 2015 ResMed Limited

GAS WASHOUT VENT FOR PATIENT INTERFACE

This application is a continuation of U.S. application Ser. No. 16/348,895, filed May 10, 2019, which is the U.S. national phase of International Application No. PCT/AU2017/051231 filed Nov. 9, 2017, which designated the U.S. and claims the benefit of U.S. Provisional Application No. 62/420,678, filed Nov. 11, 2016, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

1 BACKGROUND OF THE TECHNOLOGY

1.1 Field of the Technology

The present technology relates to one or more of the detection, diagnosis, treatment, prevention and amelioration of respiratory-related disorders. The present technology also relates to medical devices or apparatus, and their use.

1.2 Description of the Related Art 1.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveoloated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

1.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

1.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

1.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

1.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT" nasal pillows mask, SWIFT' II nasal pillows mask, SWIFT' LT nasal pillows mask, SWIFT' FX nasal pillows mask and MIRAGE LIBERTY' full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY' full-face mask); International Patent Application WO 2009/052,560 (describing amongst other things aspects of the ResMed Limited SWIFT™ FX nasal pillows).

1.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

1.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

1.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

1.2.3.4 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1$m$)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B + Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

An aspect of the present technology includes a gas washout vent for a patient interface system, the gas washout vent comprising: a housing comprising a first wall with one or more passages through the first wall, the one or more passages being configured to provide fluid communication with a portion of the patient interface system that is configured to be exposed to the therapy pressure, the housing at least partially defining a second opening that is in communication with ambient atmosphere; and a diffusing material located at least partially within the housing.

An aspect of the present technology includes a gas washout vent for a patient interface system configured to maintain a therapy pressure in a range of about 4 cmH$_2$O to about 30 cmH$_2$O above ambient air pressure in use, throughout a patient's respiratory cycle, while the patient is sleeping, to ameliorate a respiratory or a sleep disordered breathing condition, the gas washout vent comprising: a housing comprising a first wall with one or more passages through the first wall, the one or more passages being configured to provide fluid communication with a portion of the patient interface system that is configured to be exposed to the therapy pressure, the passages including respective first openings on a first surface of the first wall, the housing at least partially defining a second opening that is in communication with ambient atmosphere; and a diffusing material located at least partially within the housing to be adjacent the first surface, a surface of the diffusing material facing the first surface being spaced away from the first surface by a gap that extends to provide a fluid communication between all of the first openings, as well as between all of the first openings and the second opening; wherein the housing is configured so that air is prevented from flowing out of the housing at all areas directly opposite each of the first openings.

In examples, (a) the housing further comprises a third opening in communication with ambient atmosphere, wherein the third opening does not overlap with an area of an outlet of any of the passages that is projected along a central axis of the respective passages, and is located so that at least part of the diffusing material is between each first opening and the third opening; (b) the third opening is oriented so that a central axis through the third opening is angled with respect to the central axis of any of the passages; (c) he third opening is sized so that completely blocking the third opening does not substantially decrease the air flow through the gas washout vent when the portion of the patient interface is exposed to the therapy pressure; (d) the air flow through the gas washout vent does not decrease by more than three percent; (e) the third opening is one of a plurality of third openings; (f) the third opening is configured for water removal; (g) the second opening comprises a plurality of second openings; (h) at least one of the one or more passages is sized so that at least a portion of air exiting the respective first opening penetrates into the diffusing material when the portion of the patient interface is exposed to the therapy pressure; (i) the gas washout vent is configured so that the portion of the air penetrating the diffusing material exits the diffusing material and re-enters the gap before flowing out of the second opening; (j) the gas washout vent is configured so that the portion of the air exiting the respective first opening penetrates and exits the diffusing material via the surface; (k) no more than 28 dB(A) noise is generated when air exits the second opening as a result of the portion of the patient interface being exposed to the therapy pressure; (l) the diffusing material comprises uncompressed fibers; (m) he diffusing material comprises moisture wicking material; (n) the moisture wicking material is sintered plastic; (o) the diffusing material comprises hydrophobic material; (p) the diffusing material possesses antibacterial properties; (q) the first wall is fixed in the housing in a non-releasable manner; (r) the gap is at least partially bounded by the first wall from the first openings to the second opening; (s) the gap is formed by the surface from a location opposed to the first openings to a portion of the diffusing material that is closest to the second opening; (t) the gap is tapered in a radial direction; (u) the gap tapers off in a radially outward direction; (v) the surface of the diffusing material and the first surface are parallel; (x) the surface of the diffusing material and the first surface are inclined with respect to one another; (z) a portion of the housing is removable to allow replacement of the diffusing material; (aa) the second opening and the gap are sized so that a majority of pressure drop during the flow of air through the passages, the gap and the second opening, occurs prior to exiting the passages; and/or (bb) he gas washout vent comprises a separate apparatus arranged for engaging with a patient interface or an air circuit.

Another aspect of the present technology includes a system for treating a respiratory disorder in a patient that comprises a respiratory pressure therapy device; a humidifier; an air circuit; and a patient interface, and at least one of the air circuit and the patient interface comprises the gas washout vent according to any preceding aspect or example.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

3 BRIEF DESCRIPTION OF THE DRAWINGS

The present technology is illustrated by way of example, and not by way of limitation, in the figures of the accompanying drawings, in which like reference numerals refer to similar elements including:

3.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

3.2 Respiratory System and Facial Anatomy

Figure 1A:
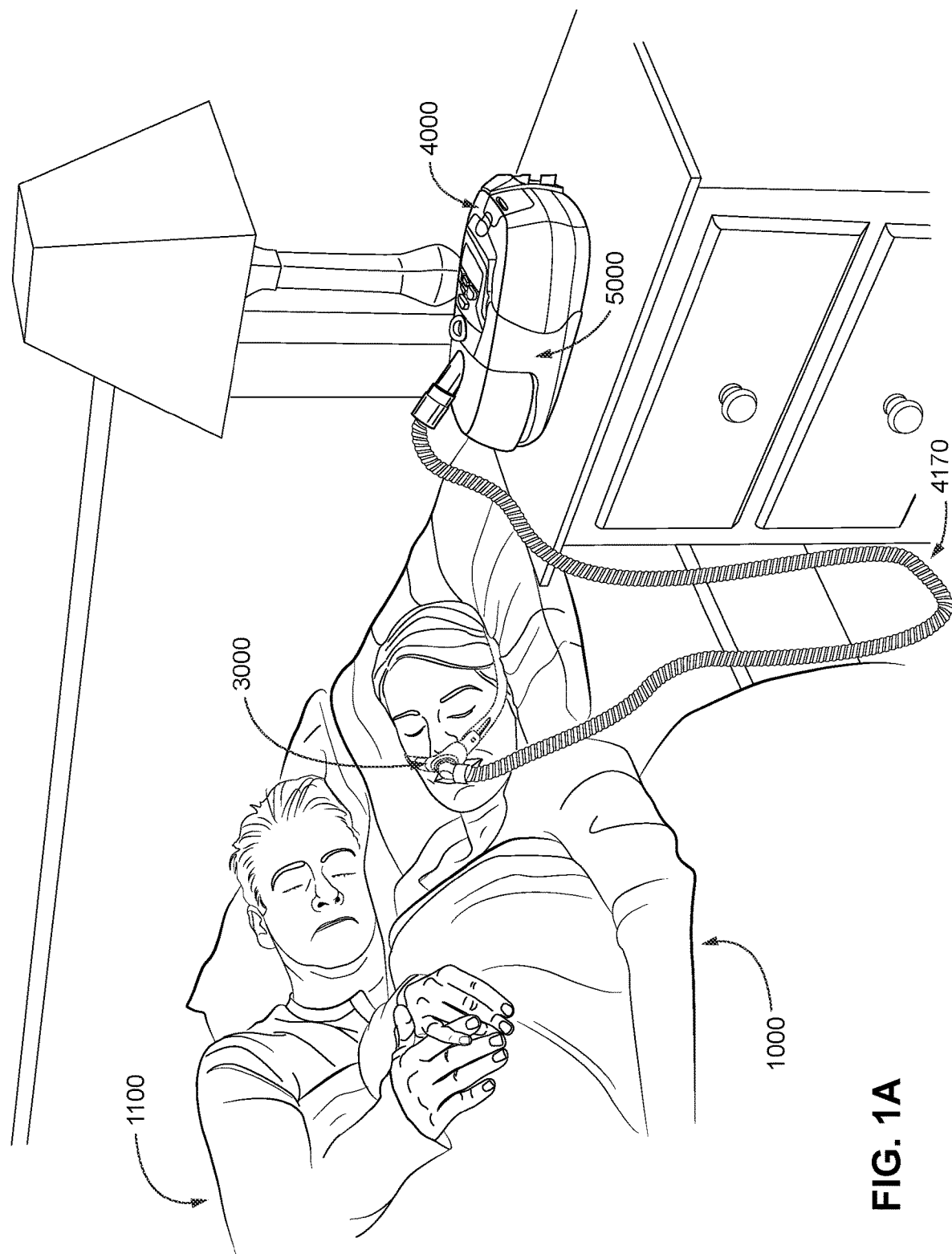
Figure 1B:
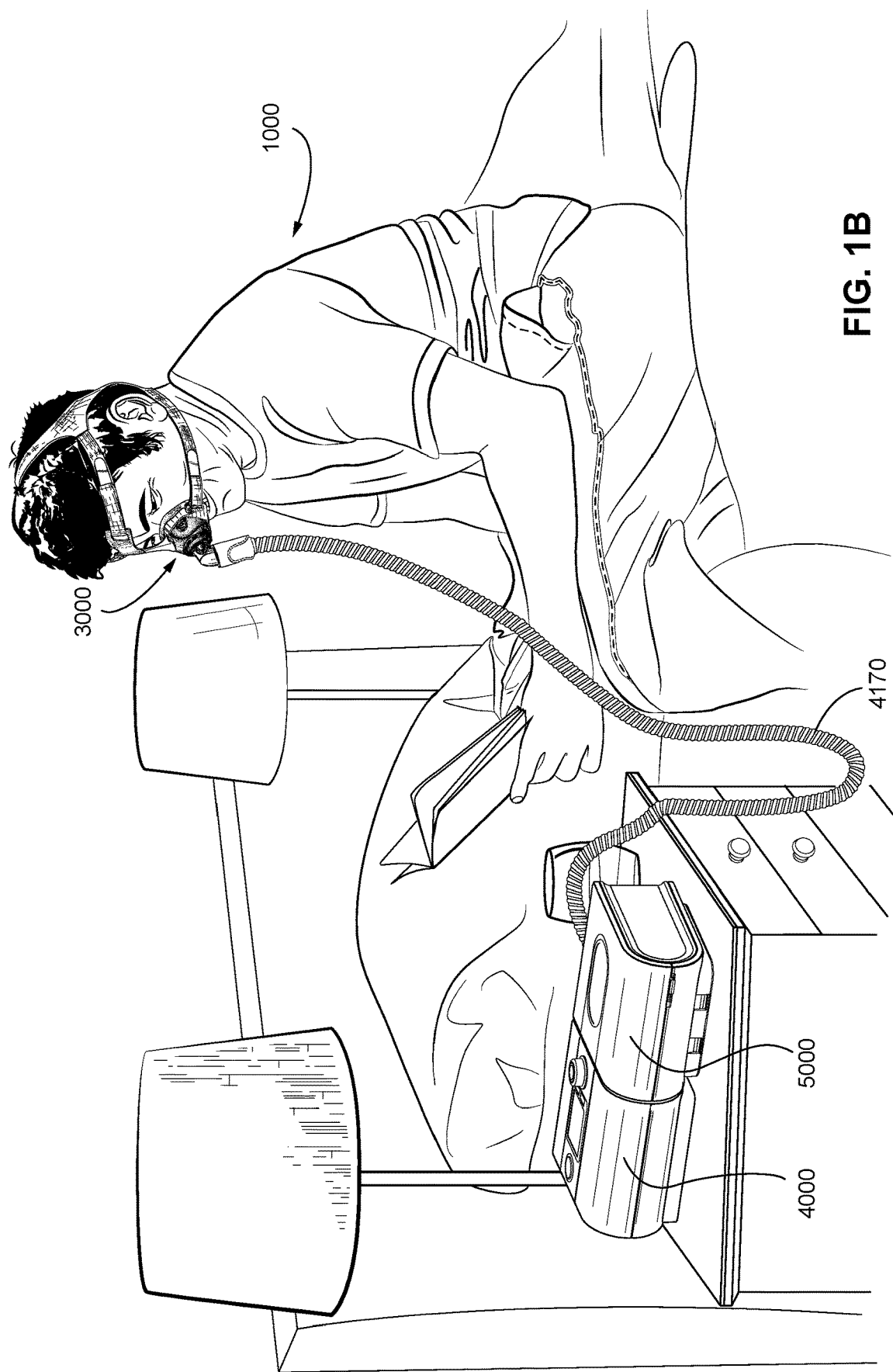
Figure 1C:
Figure 2A:
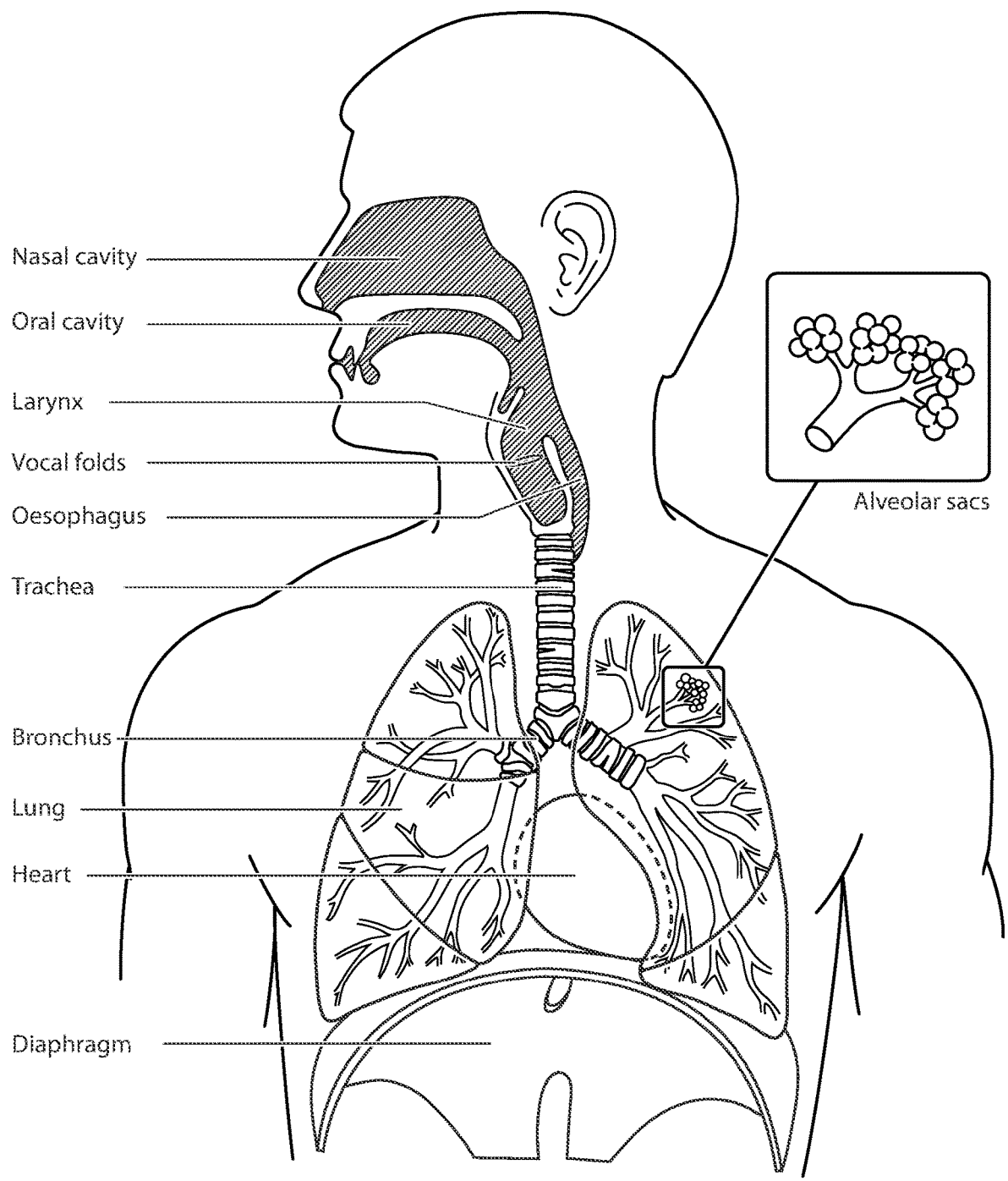
FIG. 2A shows an overview of a human respiratory system including the nasal and oral cavities, the larynx, vocal folds, oesophagus, trachea, bronchus, lung, alveolar sacs, heart and diaphragm.
Figure 2B:
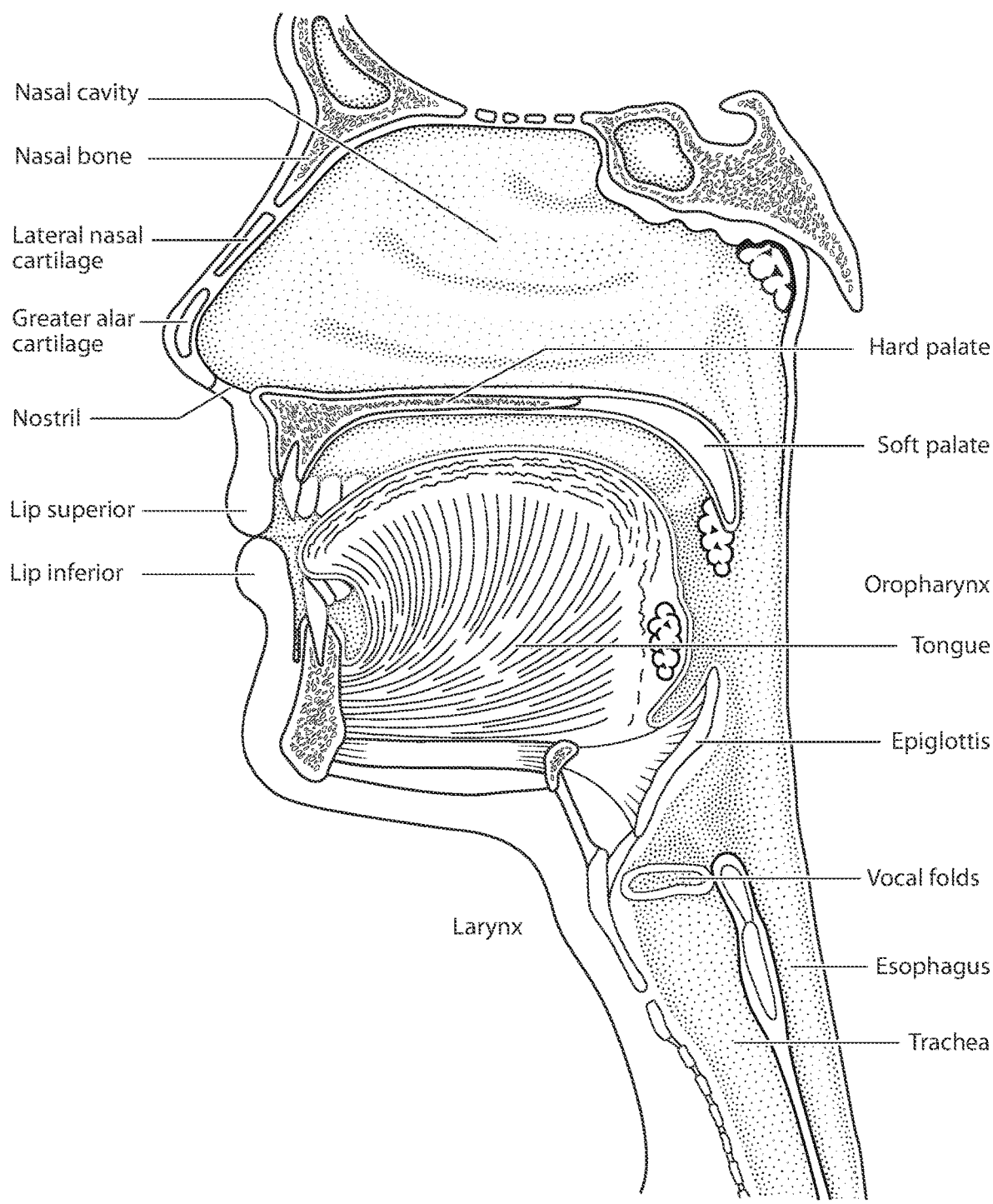
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
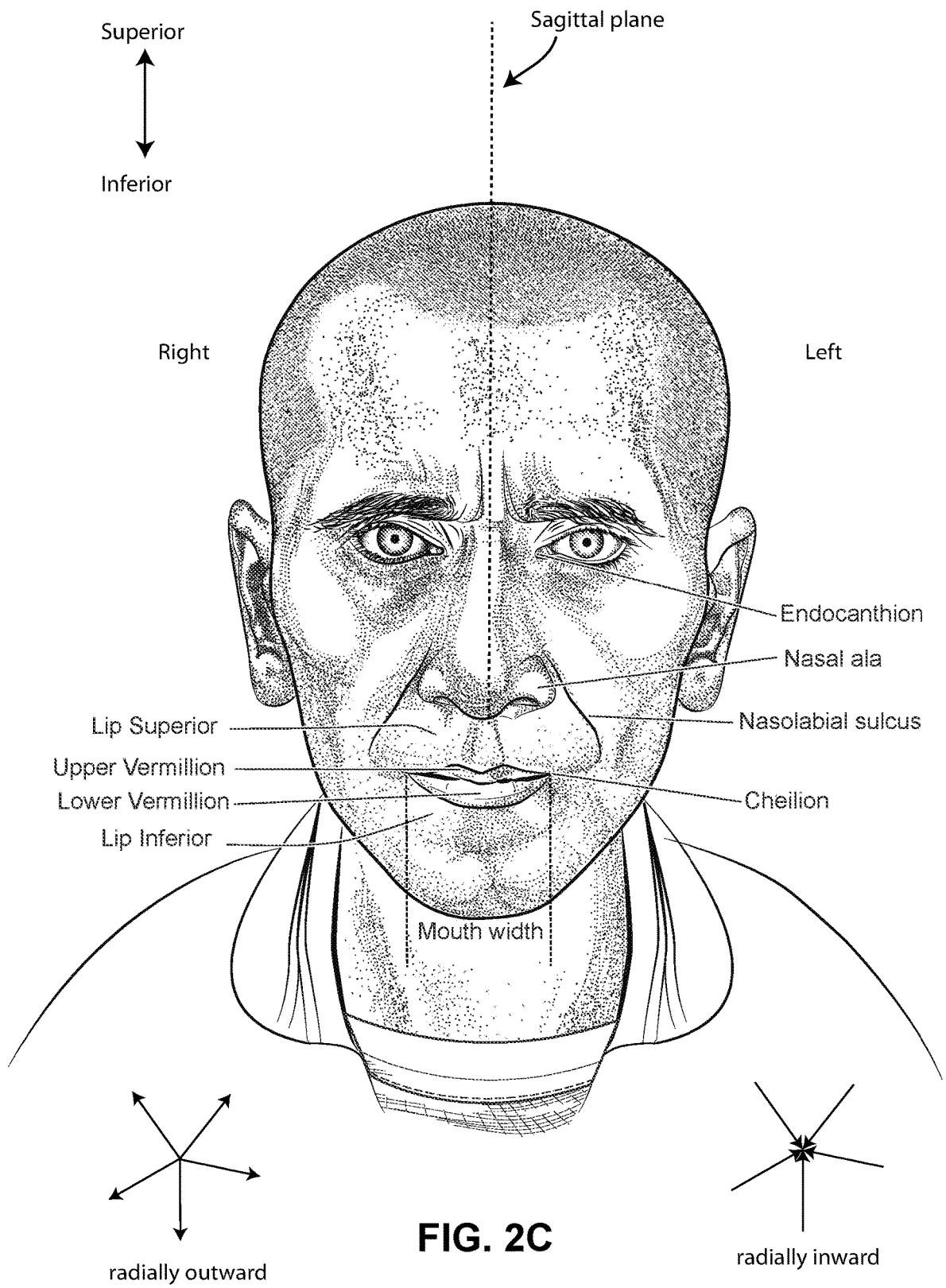
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
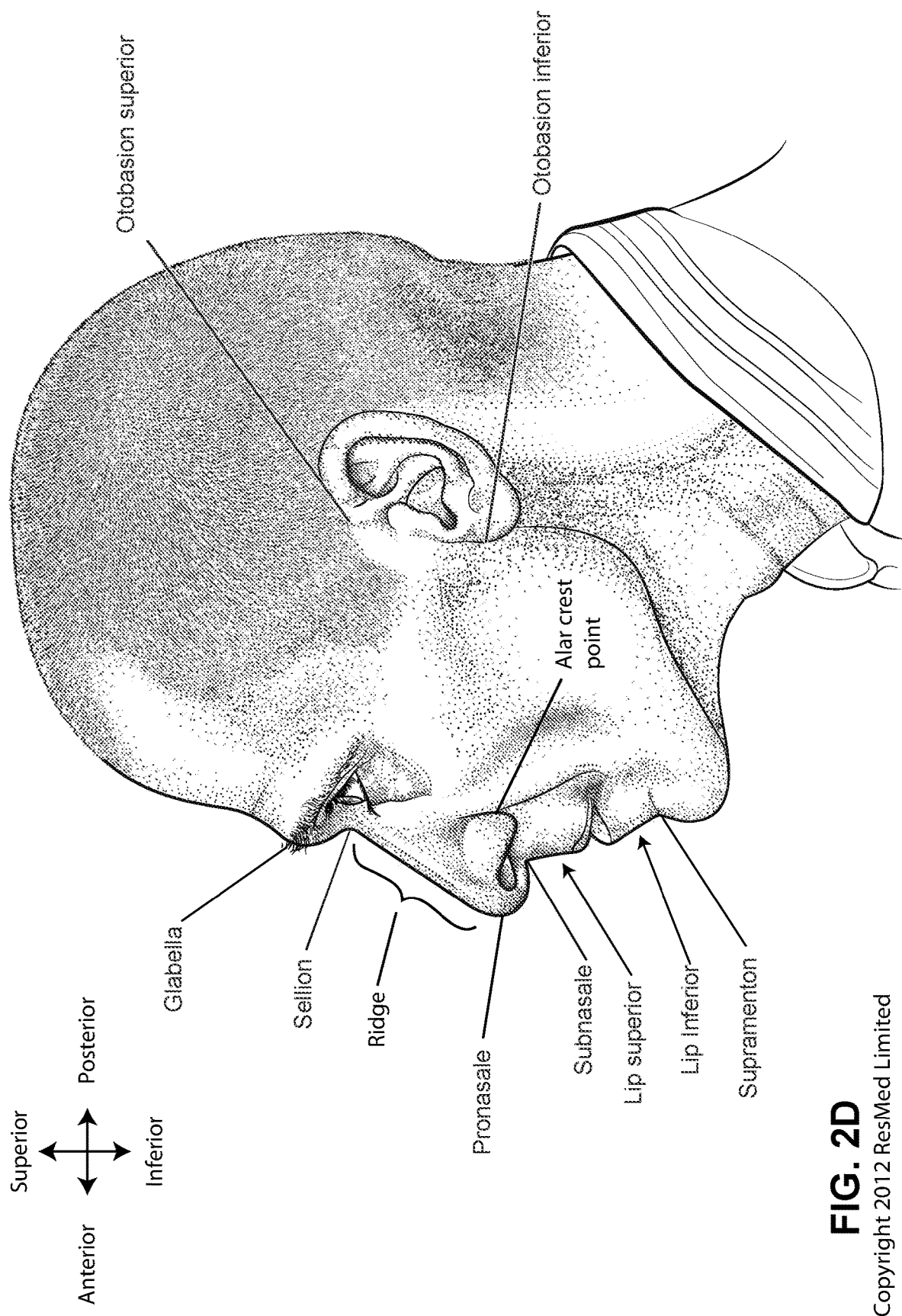
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
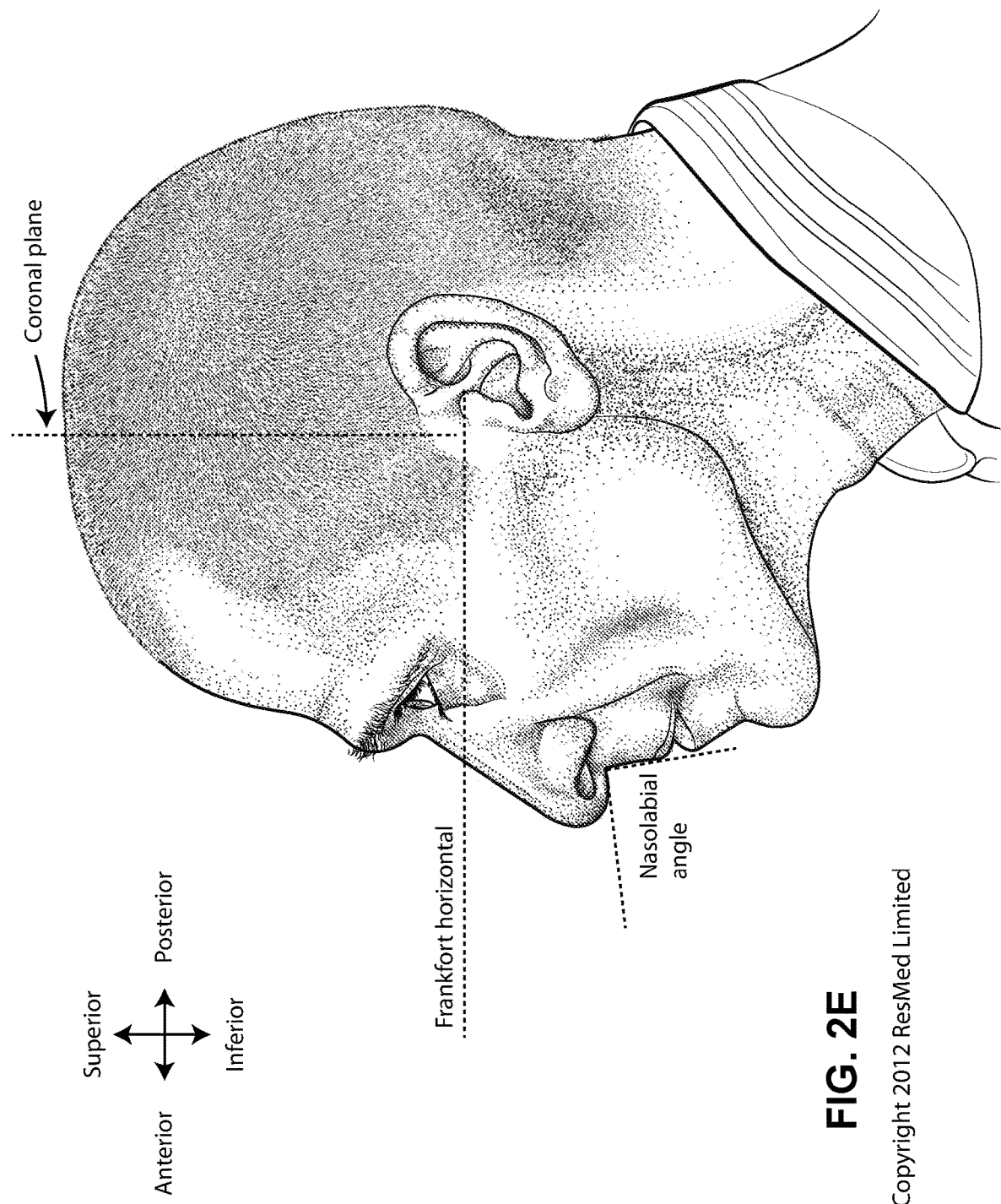

FIG. 2E is a further side view of a head. The approximate locations of the Frankfort horizontal and nasolabial angle are indicated. The coronal plane is also indicated.

Figure 2F:
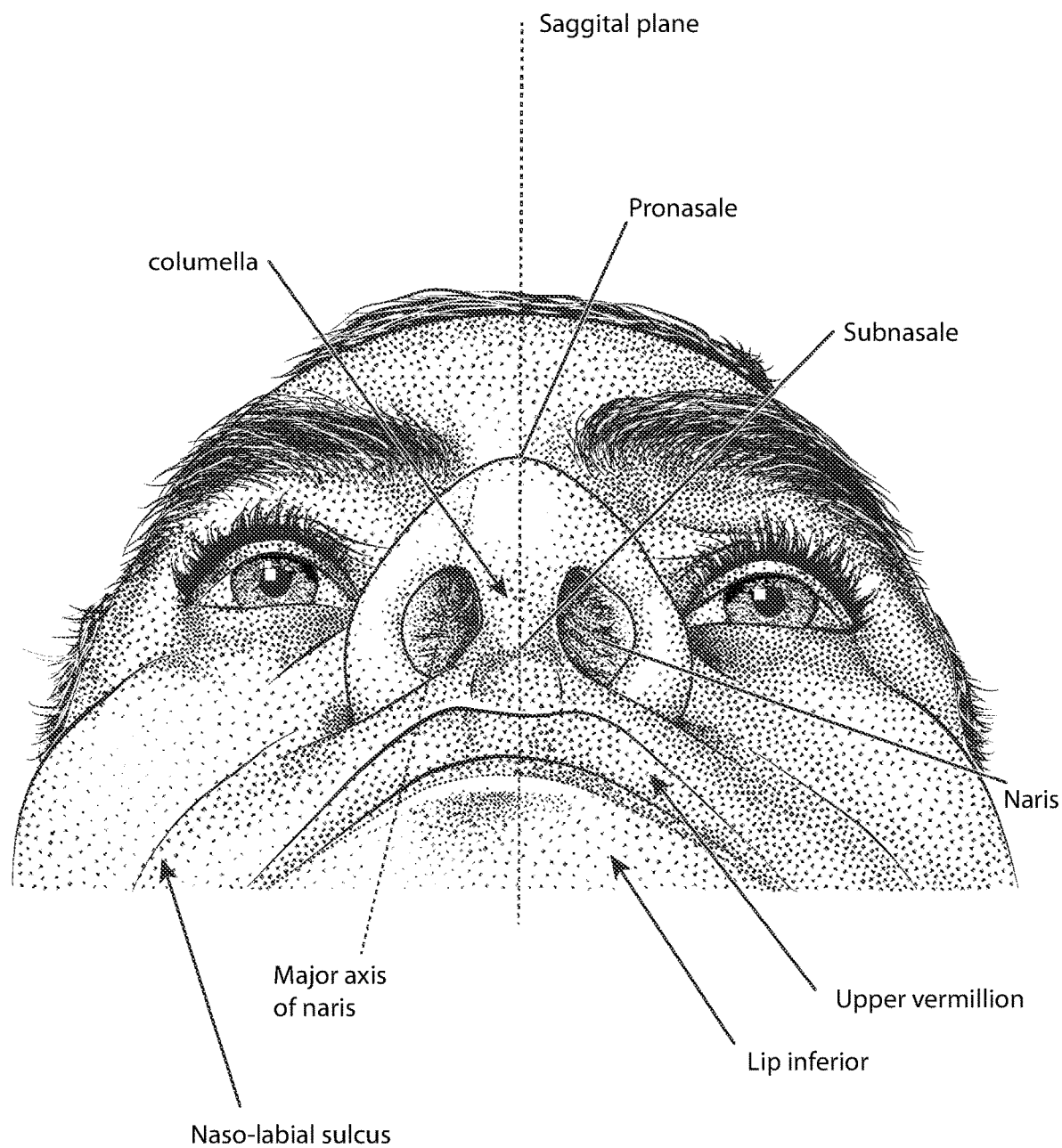

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
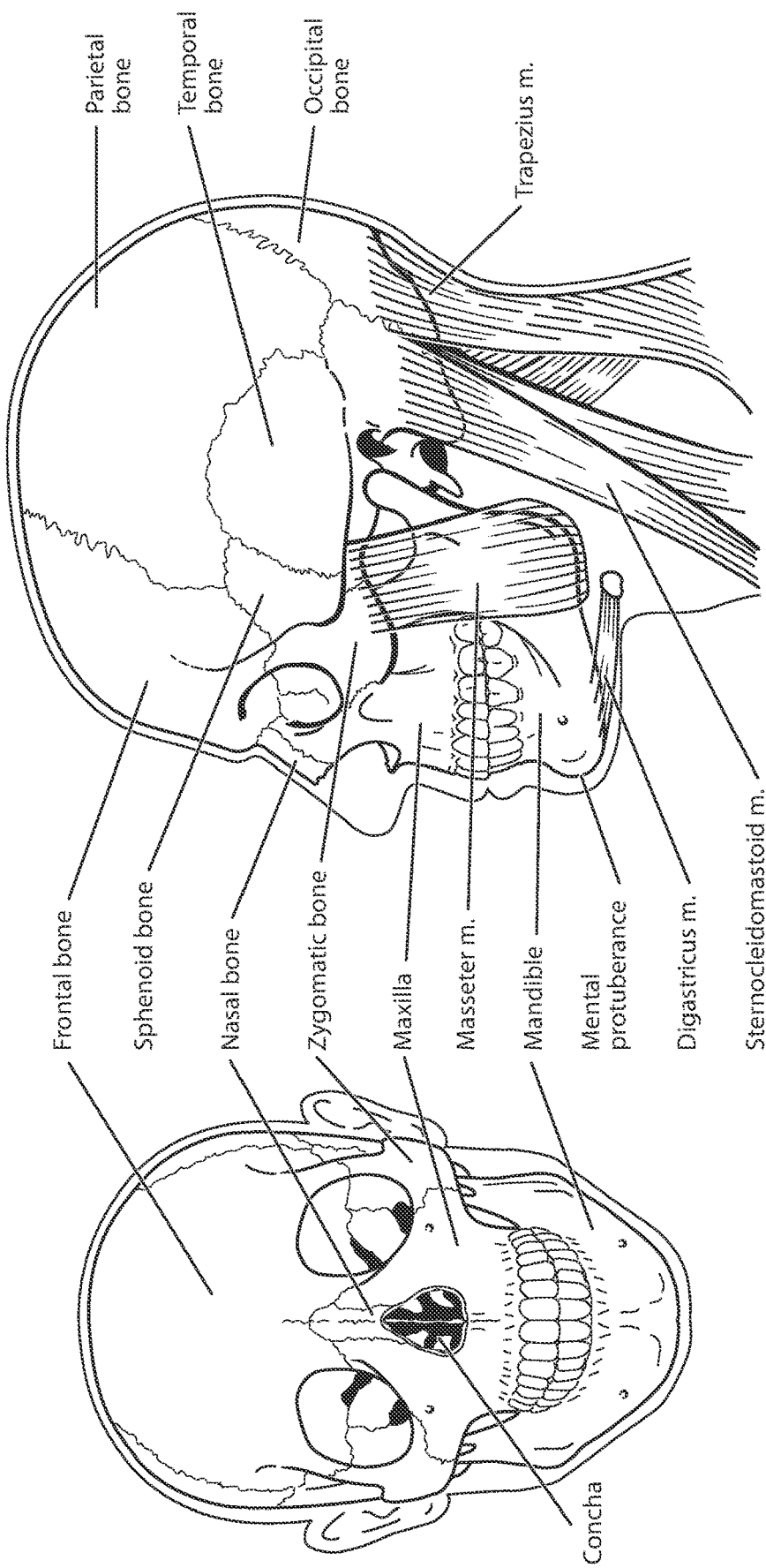

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
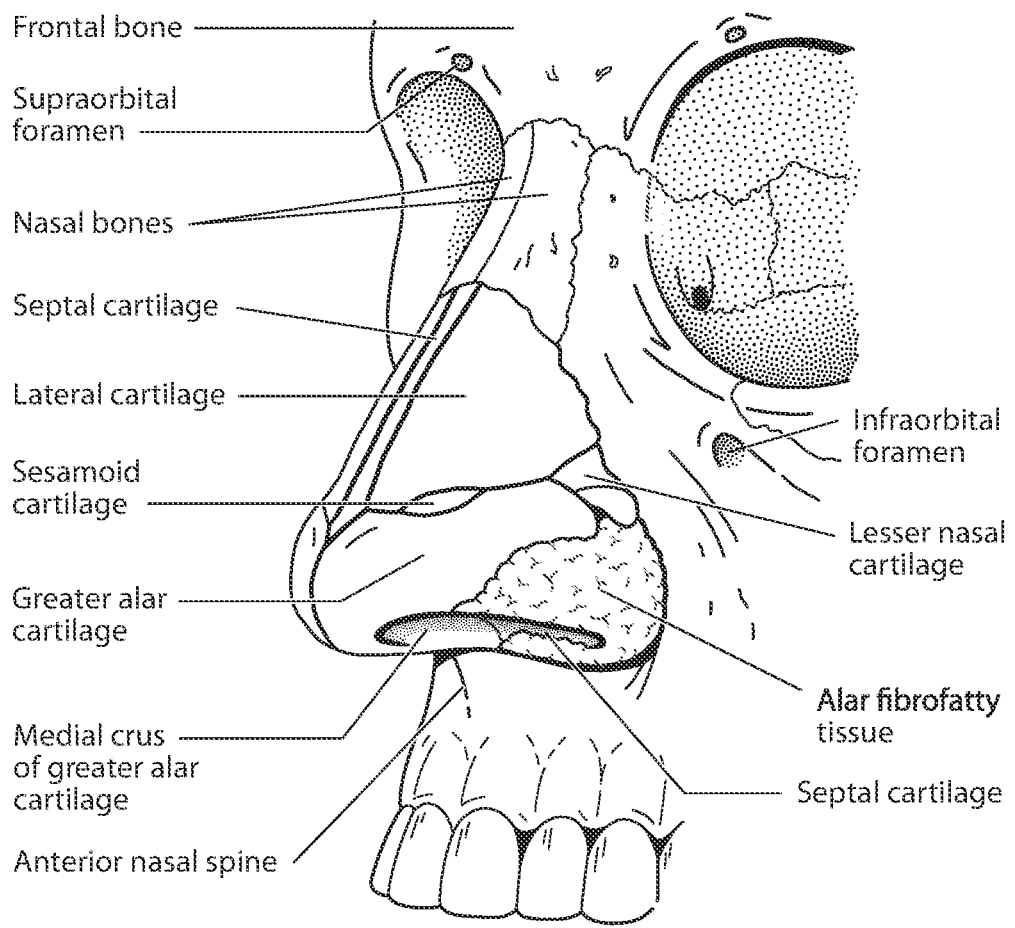

FIG. 2L shows an anterolateral view of a nose.

3.3 Patient Interface

Figure 3A:
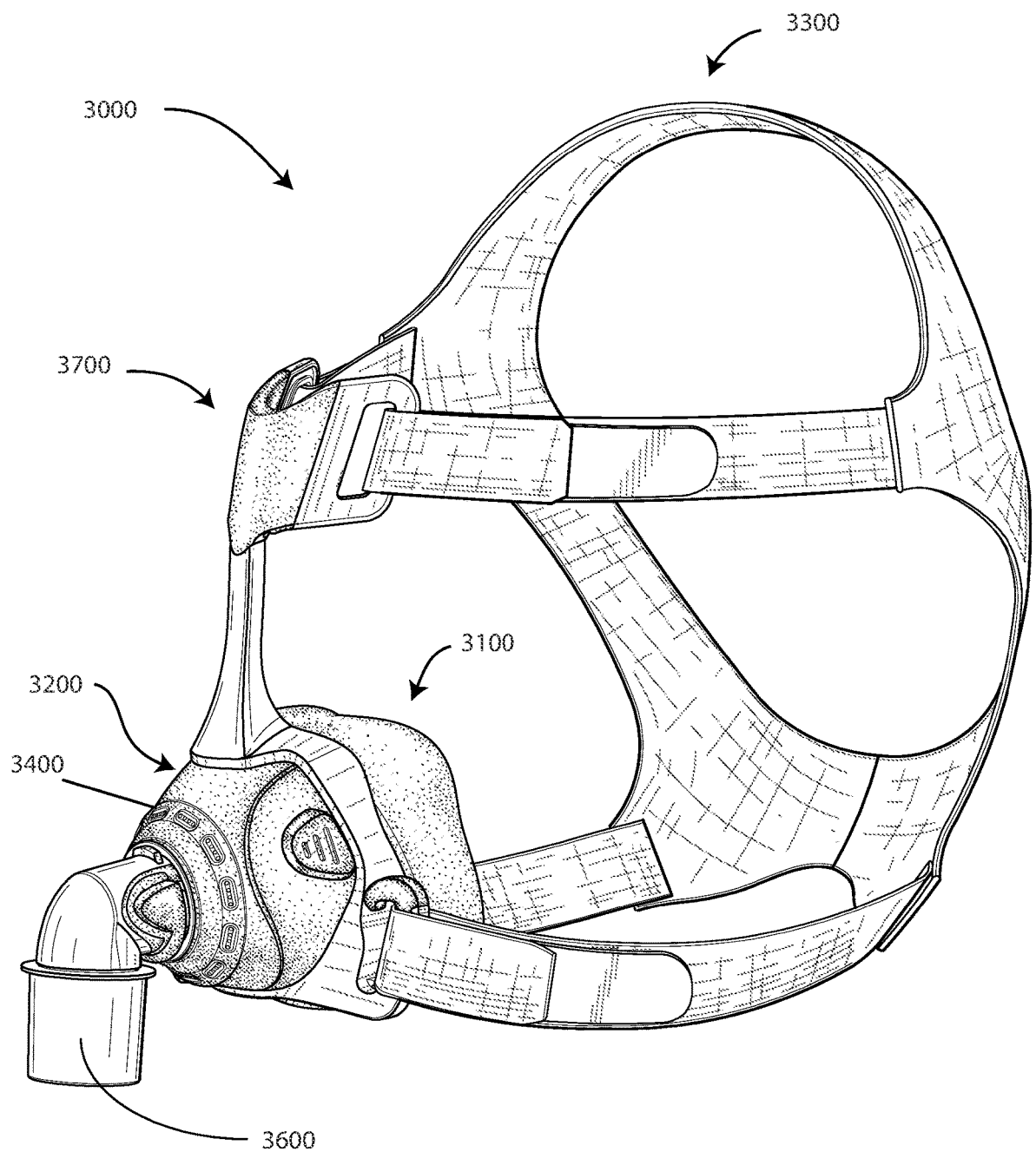

FIG. 3A shows a patient interface in the form of a nasal mask in accordance with one form of the present technology.

Figure 3B:
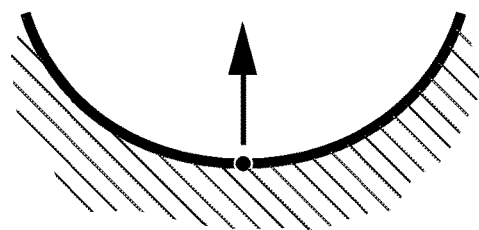

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
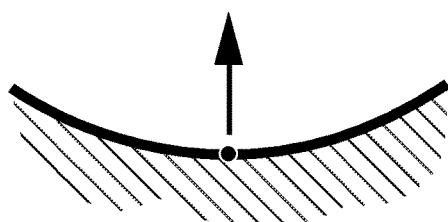

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
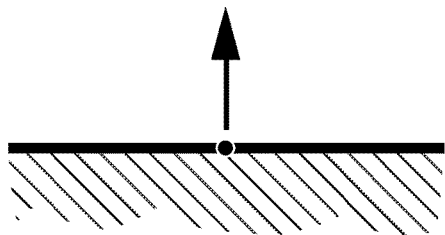

FIG. 3D shows a schematic of a cross-section through a structure at a point. An outward normal at the point is indicated. The curvature at the point has a value of zero.

Figure 3E:
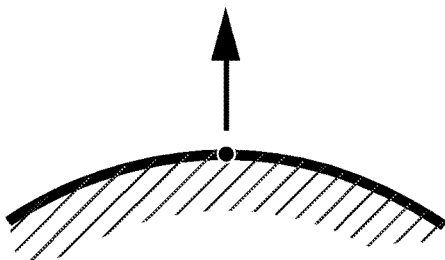

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
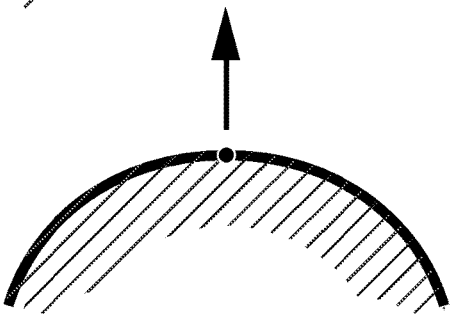

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figures 3G, 3H:
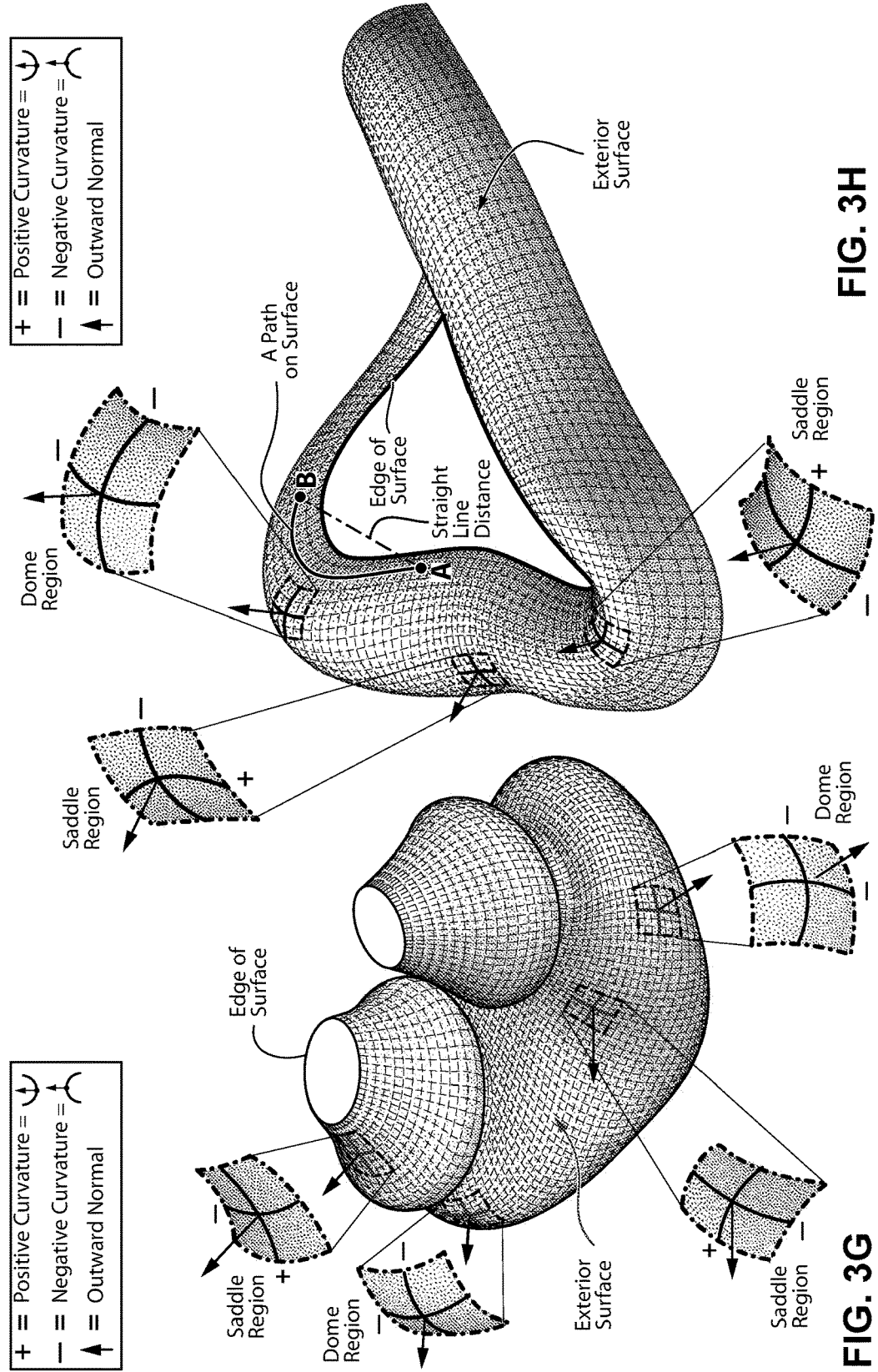

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
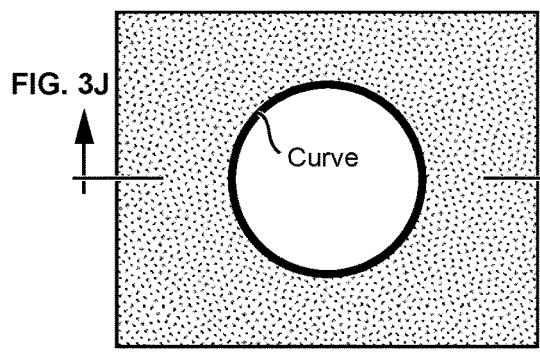

FIG. 3I shows the surface of a structure, with a one dimensional hole in the surface. The illustrated plane curve forms the boundary of a one dimensional hole.

Figure 3K:
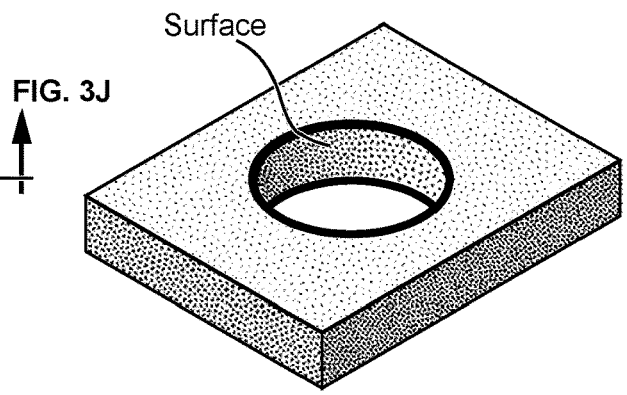
Figure 3J:
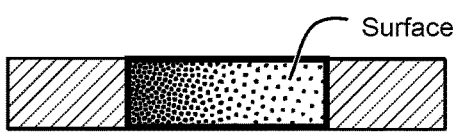

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
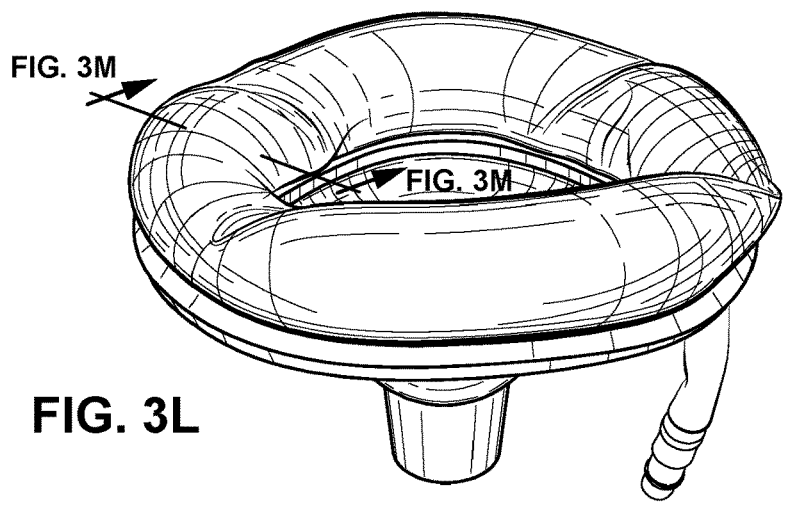

FIG. 3L shows a mask having an inflatable bladder as a cushion.

Figure 3M:
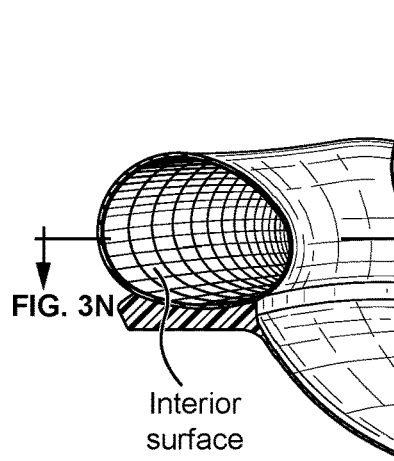

FIG. 3M shows a cross-section through the mask of FIG. 3L, and shows the interior surface of the bladder. The interior surface bounds the two dimensional hole in the mask.

Figure 3N:
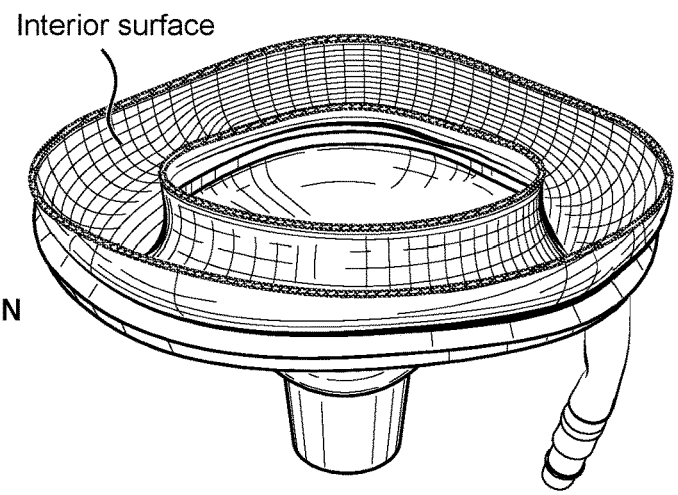

FIG. 3N shows a further cross-section through the mask of FIG. 3L. The interior surface is also indicated.

Figure 3O:
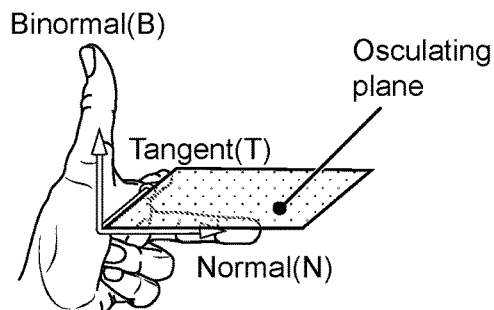

FIG. 3O illustrates a left-hand rule.

Figure 3P:
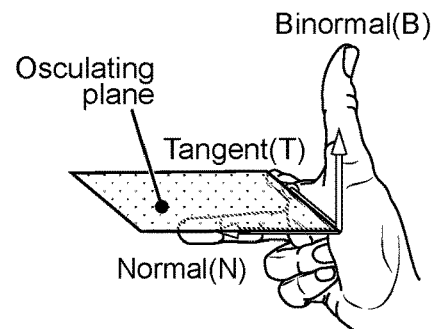

FIG. 3P illustrates a right-hand rule.

Figure 3Q:
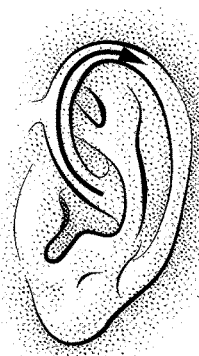

FIG. 3Q shows a left ear, including the left ear helix.

Figure 3S:
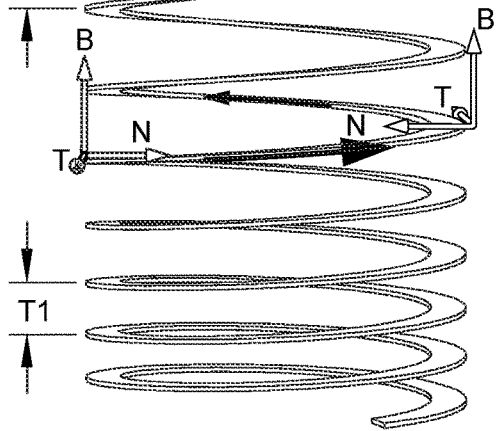
Figure 3R:
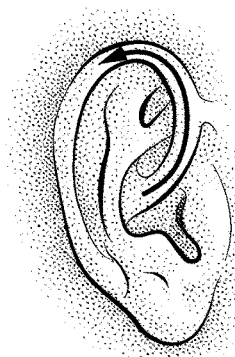

FIG. 3R shows a right ear, including the right ear helix.

FIG. 3S shows a right-hand helix.

Figure 3T:
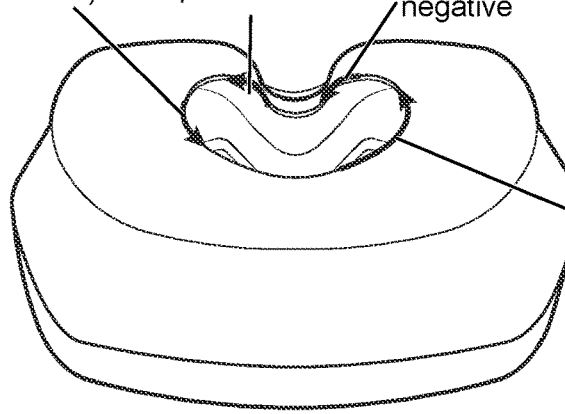

FIG. 3T shows a view of a mask, including the sign of the torsion of the space curve defined by the edge of the sealing membrane in different regions of the mask.

3.4 Vent

Figure 4A:
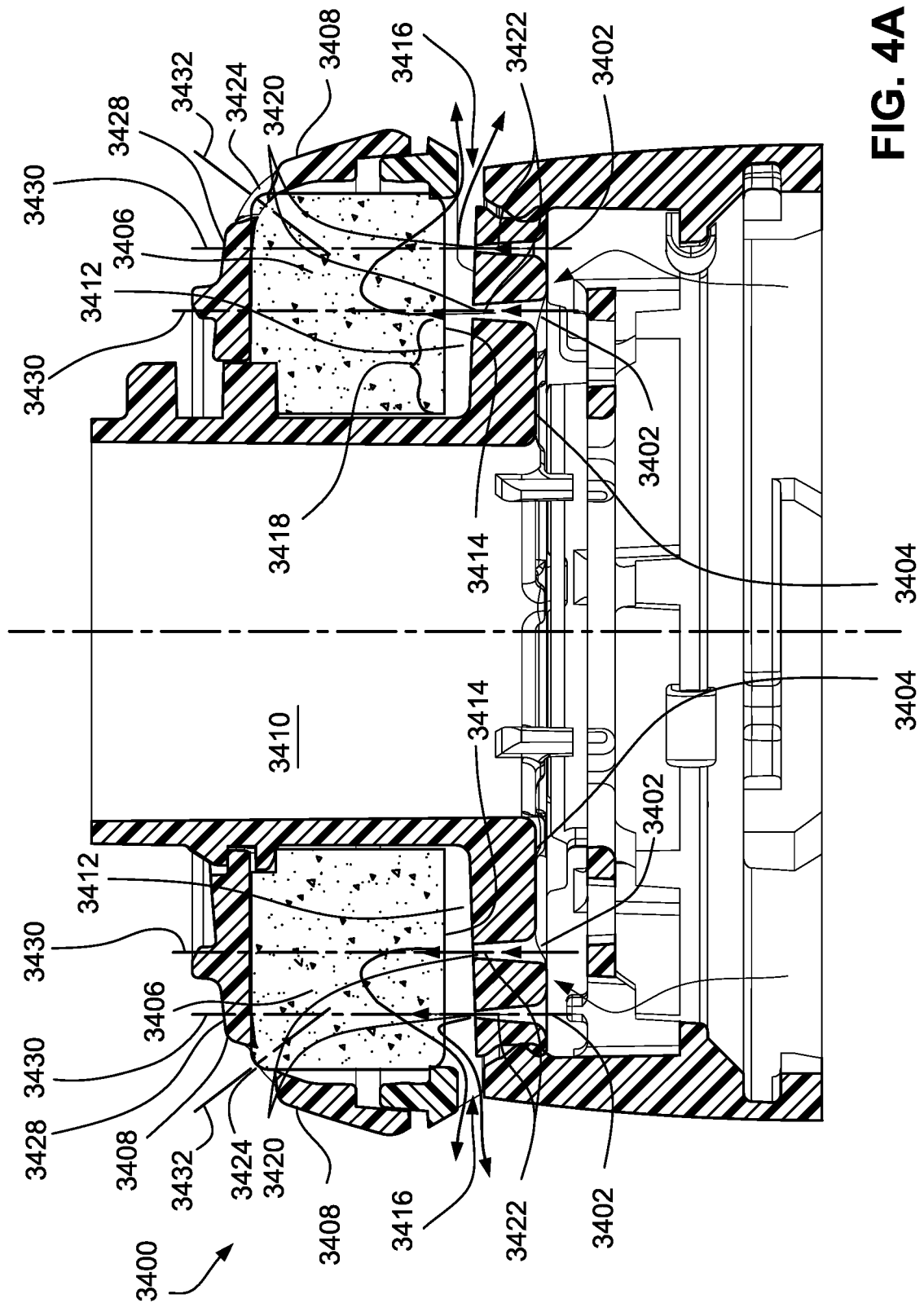

FIG. 4A shows a vent in accordance with one form of the present technology.

Figure 4B:
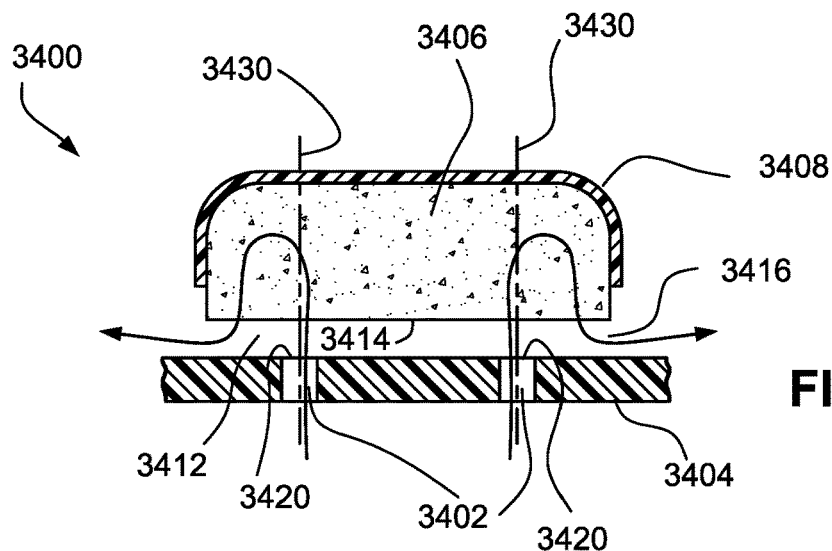

FIG. 4B show a vent in accordance with another form of the present technology.

Figure 4C:
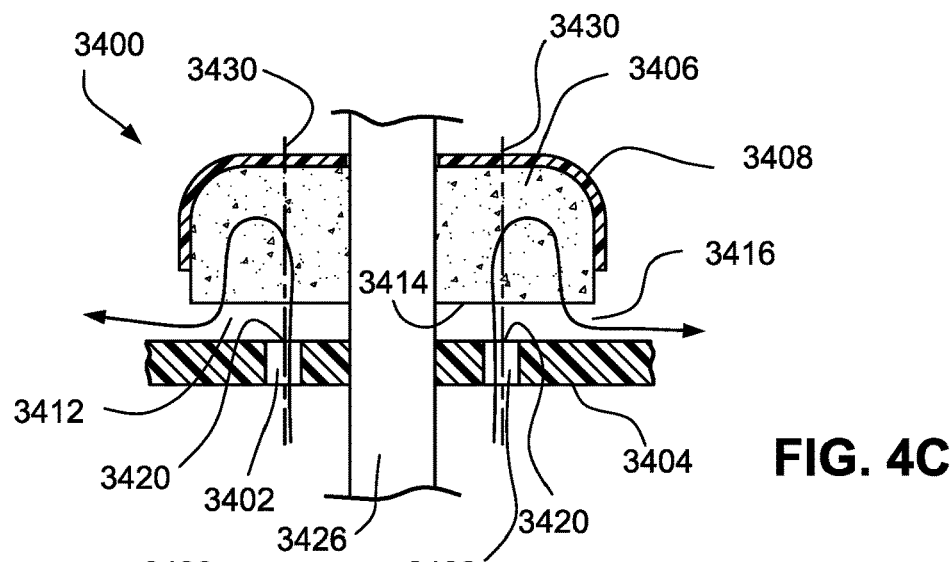

FIG. 4C show a vent in accordance with another form of the present technology.

Figure 4D:
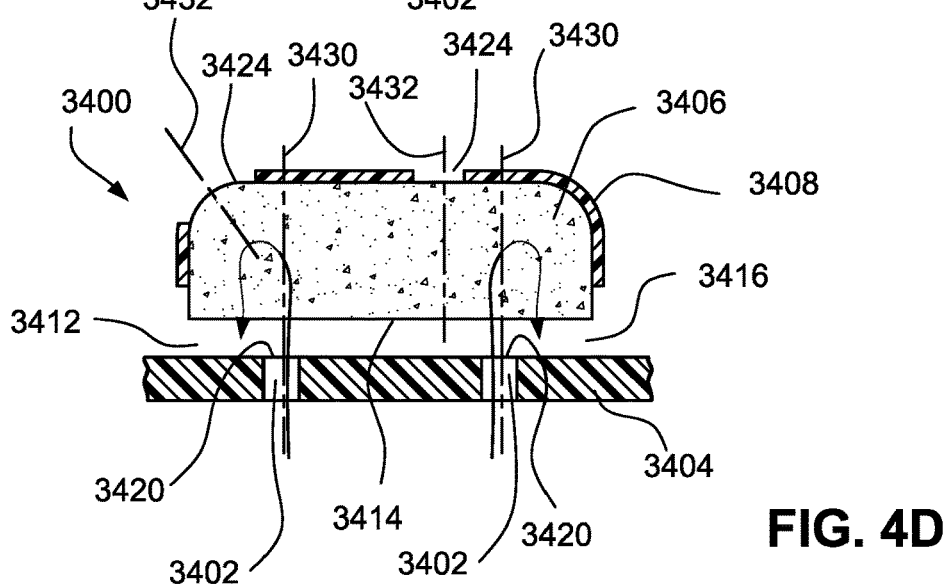

FIG. 4D show a vent in accordance with another form of the present technology.

Figure 4E:
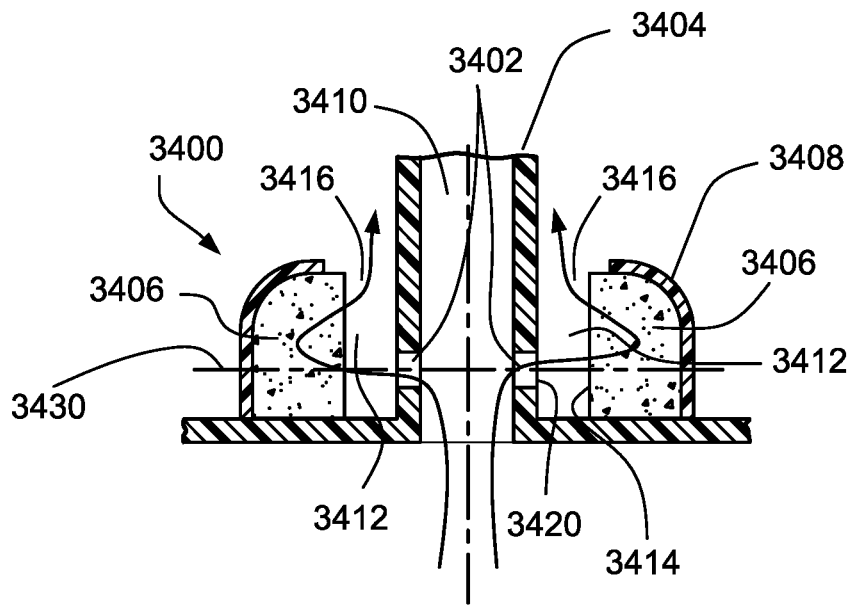

FIG. 4E show a vent in accordance with another form of the present technology.

Figure 4F:
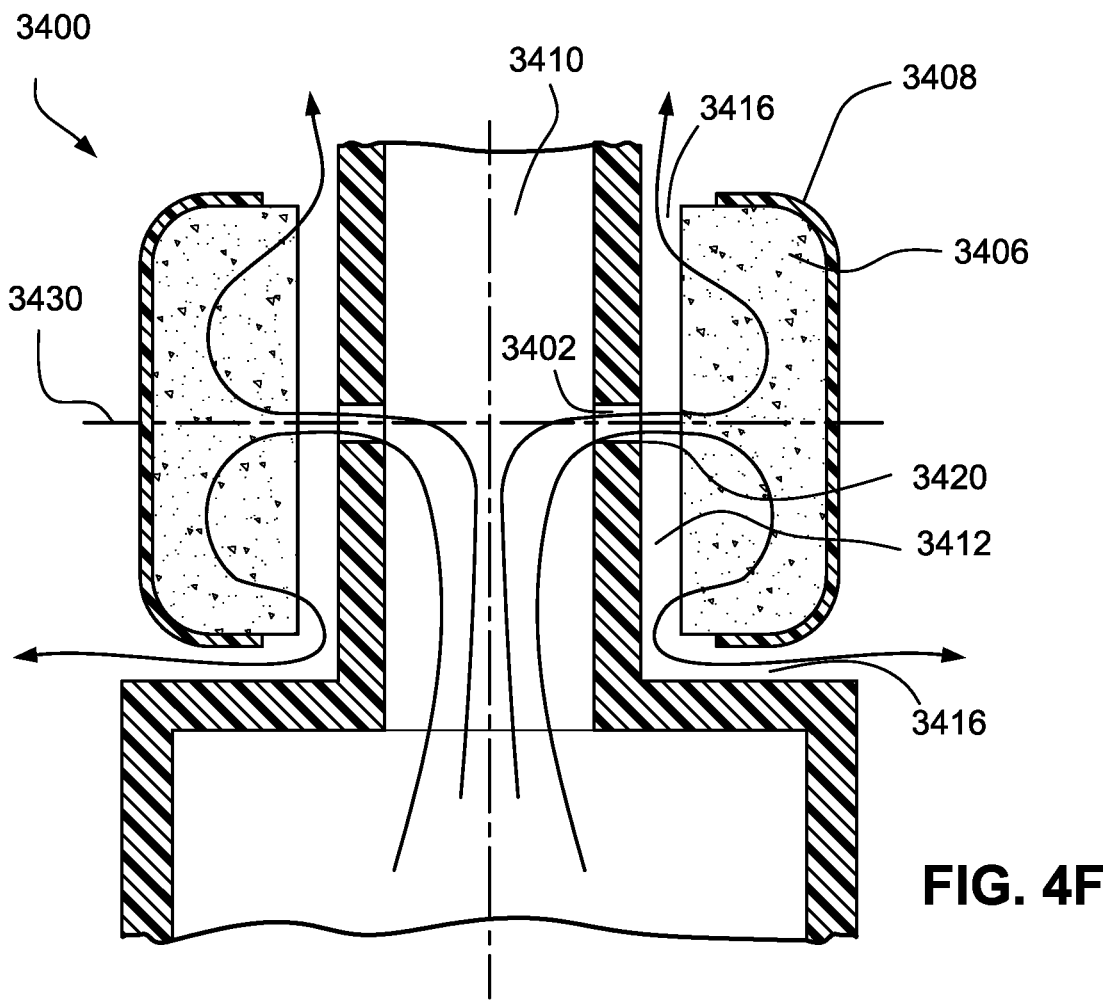

FIG. 4F show a vent in accordance with another form of the present technology.

Figure 4G:
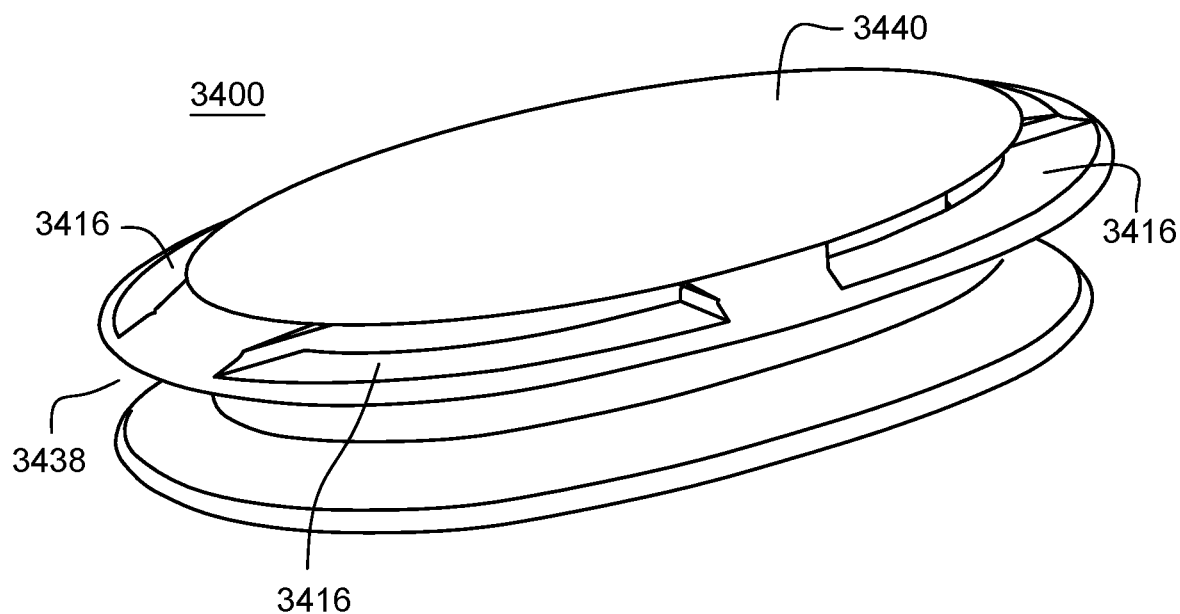

FIG. 4G show a vent in accordance with another form of the present technology.

Figure 4H:
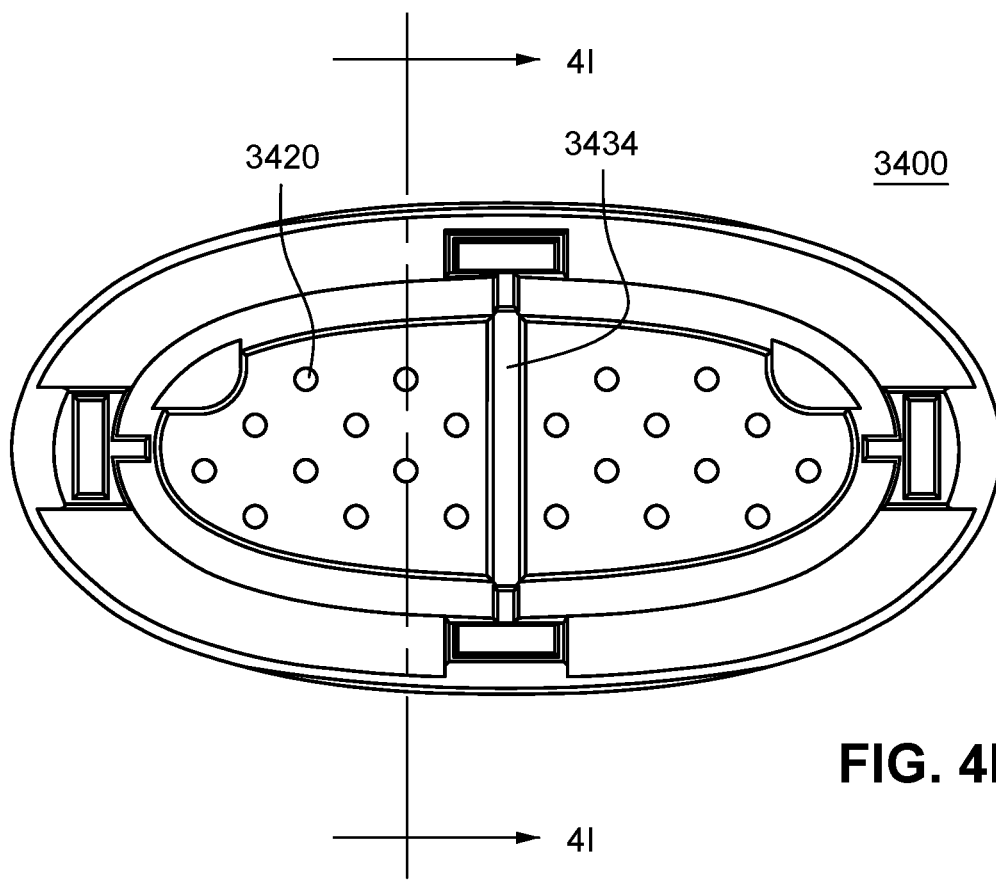

FIG. 4H show the vent of FIG. 4G with a top portion removed so that interior structure is visible.

Figure 4I:
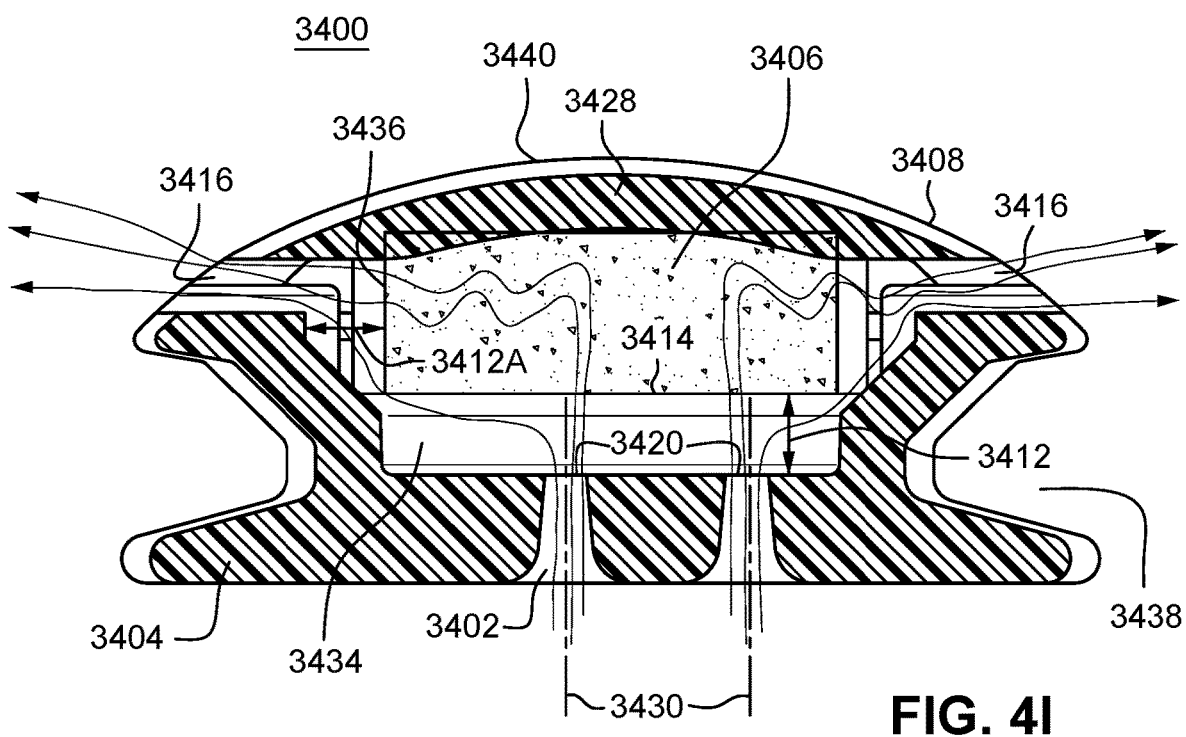

FIG. 4I show a cross-section of FIG. 4H but with the top portion included.

Figure 4J:
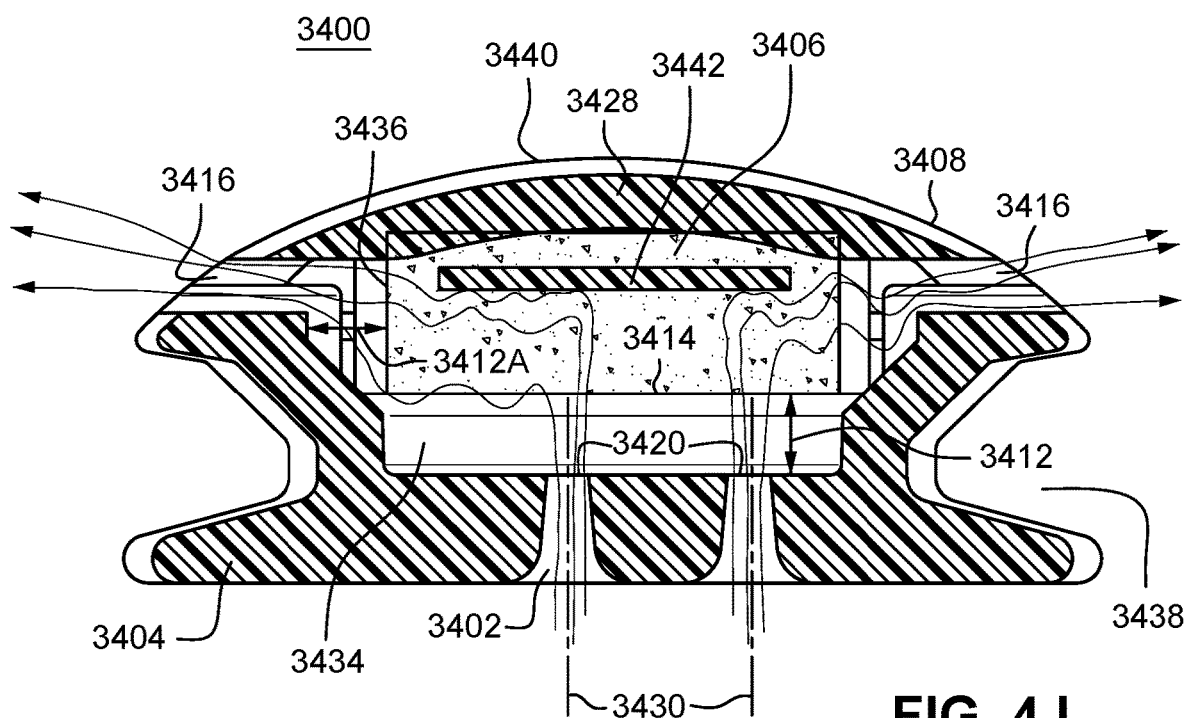

FIG. 4J show a first alternative cross-section of FIG. 4H with an additional component included.

Figure 4K:
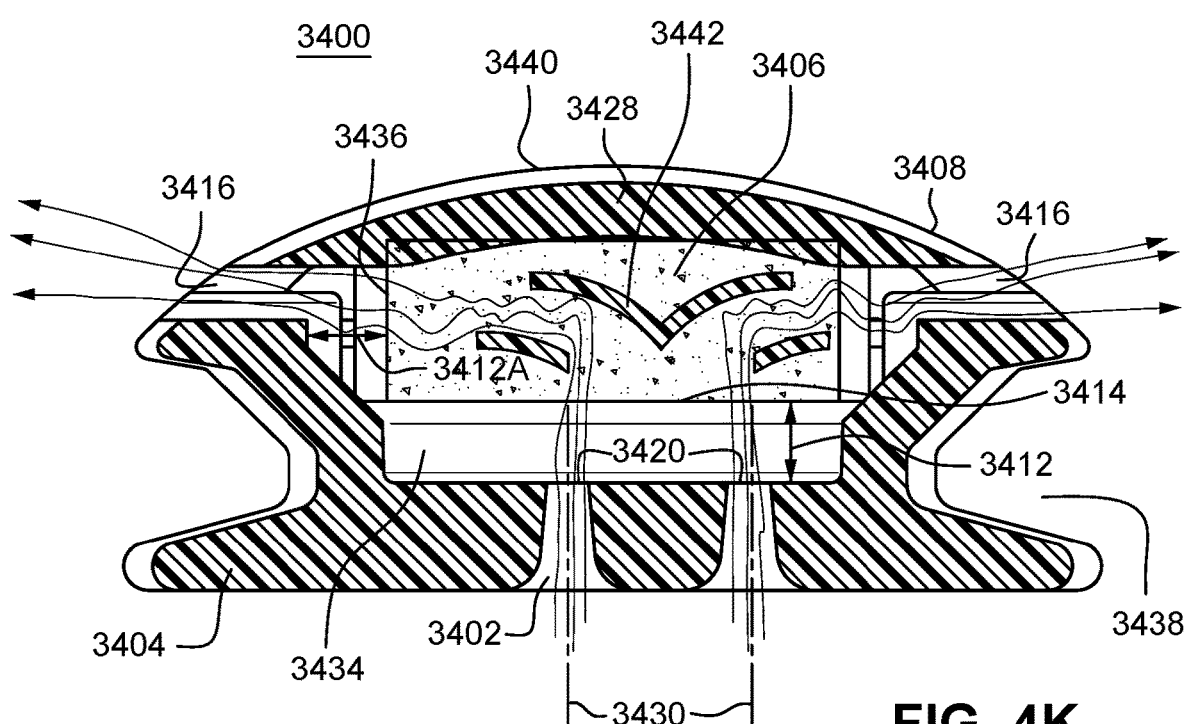

FIG. 4K show a second alternative cross-section of FIG. 4H with an alternative version of the additional component included.

4 DETAILED DESCRIPTION OF EXAMPLES OF THE TECHNOLOGY

Before the present technology is described in further detail, it is to be understood that the technology is not limited to the particular examples described herein, which may vary.

It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

4.1 THERAPY

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

4.2 TREATMENT SYSTEMS

In one form, the present technology comprises an apparatus or device for treating a respiratory disorder. The apparatus or device may comprise an RPT device 4000 for supplying pressurised air to the patient 1000 via an air circuit 4170 to a patient interface 3000.

4.3 PATIENT INTERFACE

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

4.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

4.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

4.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

4.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

4.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

4.3.1.5 Forehead Region

In one form, the seal-forming structure that forms a seal in use on a forehead region of the patient's face. In such a form, the plenum chamber may cover the eyes in use.

4.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

4.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

4.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

4.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

The vent 3400 may take various forms. In one form, vent 3400, in accordance with the present technology, comprises a plurality of holes, for example, about 20 to about 80 holes, or about 40 to about 60 holes, or about 45 to about 55 holes. The size of each hole may be between 0.5 and 1 mm, preferably between 0.6 and 0.9 mm and more preferably between 0.7 and 0.8 mm. Whilst the holes are usually formed with circular openings, other shapes are also possible. A number of smaller holes may be replaced by one or more larger holes. Some of the larger holes may have the form of slits.

The vent 3400 may be located on and integrated within the plenum chamber 3200 or within the elbow 3600. Alternatively, the vent 3400 may be formed separately as a decoupling structure, e.g., a swivel, that can be located as part of the air circuit 4170 or between the air circuit 4170 and the plenum chamber 3200.

FIG. 4A illustrates an implementation of a vent 3400 (e.g., a gas washout vent). FIG. 4A is a cross-section through passages 3402, a wall 3404, a diffusing material 3406, and a housing 3408, each of which are around a central air passage 3410. The air passage 3410 may be part of an inlet to the plenum chamber 3200 (e.g., part of a decoupling structure) or may be part of the air circuit 4170. The illustrated cross-section includes some amount of symmetry about the central air passage 3410, but symmetry is not required.

The diffusing material 3406 is spaced away from the wall 3404 by a gap 3412 and thus provides a passage with uninterrupted fluid communication between the passages 3402 and an opening 3416. This is provided by locating the diffusing material at least partially in the housing so that a surface 3414 of the diffusing material 3406 faces the surface of openings 3420. The surface 3414 of the diffusing material is a substantially planar surface and is spaced away from the surface of openings 3420 by the gap 3412. The configuration is such that the gap extends to provide fluid communication between all of the openings 3420, as well as between all of the openings 3420 and the opening 3416.

The opening 3416 provides communication with ambient atmosphere. The size of the gap should be such that it would allow any dust accumulated in the gap to be cleaned and any accumulated water to be dried out. Thus the gap 3412 can be between 1 and 3 mm deep, preferably between 1.5 and 2.5 mm and even more preferably, about 2 mm. As it would be discussed later in the text, the arrangement is such that during the standard operation of the patient interface, at least some pressurised air exiting the passages 3402 (for example, a jet or pressure wave) bridges the gap 3412 and enters the diffusing material 3406. Once the airflow enters the diffusing material, the nature of the material forces the airflow onto a tortuous path. The air may enter the diffusing material 3406, even though a path of lower resistance exists via the gap 3412, if a jet of air, which may be at or approaching sonic velocity, imparts sufficient momentum on the air that at least some molecules enter the diffusing material.

The properties of the diffusing material 3412, such as thickness or density, as well as the size of openings 3424, are chosen so that the openings 3424 have a negligible effect on the overall airflow. Also, a second wall 3428 is directly opposite the passages 3402 with respect to the diffusing material 3406. Thus the housing 3408 is essentially closed for the airflow on that opposite side. Because of that, the airflow that enters the diffusing material 3406 is forced to eventually return back into the gap 3412 and out to the ambient air via the opening 3416. The tortuous path forced on the airflow by the above described configuration of the vent substantially reduces the jetting effect and/or noise generated by the jetting effect associated with the vent. Alternatively or additionally, because the diffusing material 3406 defines at least one side of the gap 3412, any sound waves propagating through the gap will be able to expand into the diffusing material 3406 and reduce the sound level, even if there is little or no net flow of air through the diffusing material 3406 itself.

As illustrated, the gap 3412 extends all along a surface 3414 of the diffusing material 3406 to the opening 3416, but the gap 3412 need not extend along this entire length. For example, there could be no gap at a portion 3418 (e.g., interior to a passage 3402 closest to the air passage 3410, which is radially inward in the illustrated implementation).

Other configurations of the gap 3412 that provide an uninterrupted path from the passages 3402 to the opening 3416 may also be provided.

With the gap 3412, the performance characteristics of the vent 3400 may be improved compared to a vent without the gap. For example, some materials suitable for the diffusing material 3406 may be difficult to manufacture with consistent density and air permeability. This may cause an unwanted variation in the washout airflow through the vents of different patient interfaces. The introduction of the gap offers a permanent escape path and results in a more consistent and/or predictable washout flow. The gap offers a further advantage when the airflow through the diffusing material 3406 is reduced or prevented for any reason, such as if the material 3406 has become wet. In this case the gap 3412 offers an escape path for the air to the ambient atmosphere.

The wall 3404 separates the diffusing material 3406 from an interior portion of the patient interface 3000 that is exposed to therapy pressure during use. The passages 3402 are illustrated as being through the wall 3404 and include respective openings 3420 adjacent to and facing toward the diffusing material 3406. The passages 3402 may be any number and of any geometric configuration that provides the desired flow characteristics of the vent 3400. For example, the passages could be cylindrical passages, frusto-conical passages and/or any other three-dimensional shape (such as a slot) that provides desired performance characteristics of the vent 3400. Whilst in FIG. 4A the passages are of a frusto-conical shape with a tapered down opening oriented towards the diffused material, this does not have to be the case and the tapered down opening of the frusto-conical shape may be oriented in the opposite direction. Any or all of these configurations may provide fluid communication with an interior portion of the patient interface 3000 that is configured to be exposed to the therapy pressure. A single passage 3402 may be provided, or a plurality may be provided, but providing a plurality may reduce any audible sound generated. The passages 3402 may be passive or part of a valve system (not shown) that regulates flow through the passage based on conditions such as therapy pressure. The openings 3420 and/or the passages 3402 are sized, and the openings 3420 and the diffusing material 3406 are oriented, so that air exiting the openings 3420 may impinge on the diffusing material 3406 at the surface 3414 when an interior portion of the patient interface 3000 is exposed to the therapy pressure. Air exiting the openings 3420 may also impinge when the interior portion is exposed to pressures lower than the therapy pressure. With this configuration, at least a portion of air exiting an opening 3420 may penetrate into the diffusing material 3406 when the interior portion of the patient interface 3000 is exposed to the therapy pressure, and then exit from the surface 3414 before exiting the vent via the opening 3416. Any portion of air that penetrates the diffusing material 3406 but that does not exit the surface 3414 may exit the diffusing material 3406 elsewhere due to leaks in the housing 3408. This flow configuration may result in the overall flow path for gas exiting the vent 3400 being more tortious, and therefore more likely to dampen or eliminate noise generated. Air may impinge but not penetrate if the velocity is sufficiently low and the porosity of the surface 3414 is such that surface effects prevent the air from penetrating. In this scenario, the diffusing material 3406 may still provide reduction in the jetting effect, as well as a noise reduction by allowing sound waves to propagate into the diffusing material 3406 and dissipate.

The diffusing material 3406 may cause diffusion of air as the air passes through the material, which may absorb the energy and/or reduce the air velocity. Reducing the velocity of flow reduces the associated noise, which is often due to turbulence of flow or air jets colliding with hard surfaces. The diffusing material 3406 may be fibrous material similar to that used in filter media (e.g., uncompressed fibres, such as polyester fibres) or open-celled foam. Any material that allows at least partial penetration by the air flow and that provides a tortious path for air flowing through the material may be used for the diffusing material 3406. The diffusing material can be a moisture wicking material such as sintered plastic. The diffusing material may also be hydrophobic and may be processed to have antibacterial properties. One or more of these configurations may aid with removal of moisture, which may be beneficial during cleaning.

The housing 3408 may have any shape that facilitates the retention of the diffusing material 3406 in place while also providing the desired flow characteristics of the vent 3400. The housing 3408 is illustrated to include a wall configuration that prevents air from flowing out of the housing at all areas directly opposite each of the openings 3420. The housing 3408 may include all of the structural components that surround the diffusing material 3406 such as the wall 3404 and the wall 3428. A center line 3430 is illustrated along a central axis of each of the passages 3402 and extends to the second wall 3428. If the passages are sufficiently long relative to inlet flow conditions, a fully developed flow will occur and the arrows 3422 will be approximations of flow vectors through and exiting from the passages 3402. The chaotic nature of fluid flow may result in the actual flow diverging and dissipating as the flow moves away from the passages 3402. However a vector, e.g., a magnitude and direction, may be used to characterize the flow at a given point. If these vectors are extended they will eventually intersect a portion of the housing 3408 that is devoid of openings. However, it is not only the flow vectors that generally extend along the central axes of the respective openings, which if extended in the direction of the flow will encounter a solid wall. If the cross-sectional area of each of the openings 3420 is projected along the respective center line 3430, the image of the area will be projected over a solid portion of the wall 3428 instead of an opening in the wall 3428. Thus no opening (e.g., the second opening 3424) in the housing 3408, or vent 3400, is in-line with an exit vector or overlaps with a projected area from any of the passages 3402 and air exiting the passages 3402 cannot exit the vent 3400 from a portion of the second wall 3428 that is directly opposite the passages 3402. Instead, the exit opening 3416 extends in a direction that is at an angle with respect to the passage 3402 flow vectors. The angle could be acute, but in some examples it is straight (e.g., a right angle to the exit vectors) or even obtuse. Such a configuration increases the likelihood that air exiting the passages 3402 will follow a tortious path through the diffusing material 3406 to exit the vent 3400 through openings 3416. As was mentioned before, the exit opening 3416 may be defined by one or more of the following: walls of the housing 3408, a surface of the diffusing material or a surface of another component. The exit opening 3416 could be oriented in any direction, as long as it releases the air into the ambient environment along a path that does not pass through the diffusing material 3406. In one alternative example, the flow out of the exit opening 3416 can be parallel to, but offset from, the arrows 3422.

As illustrated, the housing 3408 partly bounds the opening 3416 and the wall 3404 also partly bounds the opening 3416, but the opening 3416 can be bounded completely by the housing 3408 or not bounded at all by the housing 3408. In the latter case, the opening 3416 can, for example, be defined by a component other than the housing 3408. Any configuration and location of the opening 3416 that provides the appropriate flow path, including the gap 3412, may be utilized. As illustrated, the opening 3416 is an annular gap all around the periphery of the vent 3400, but the opening 3416 may be any number of openings. For example, it may be desirable to divide the opening 3416 into a plurality of openings to increase the stability of the resultant openings. As illustrated, the opening 3416 may be described as a direct exit to ambient, but the opening 3416 could be a less direct, or more tortious, path to ambient. For example, there could be additional structural elements that result in the flow path including one or more turns before exiting to ambient. Also, the opening 3416 could be at a different orientation with respect to the gap 3412 or wall 3404 than illustrated. As illustrated the flow path through the opening 3416 is substantially a right angle to the passages 3402 and/or arrows 3422, but the opening may be at other angles or orientations. For example, the flow path through the opening could be at an obtuse or acute angle to the passages 3402 or could be parallel to and offset from the passages 3402.

The housing 3408 may also include openings 3424 that are not in-line with the passages 3402. The openings 3424 are illustrated with a center line 3432 on the central axis of the openings 3424 to visually clarify the orientation of the openings 3424. The center lines 3430 of the passages 3402 are not aligned with the center lines 3432 of the openings 3424. The openings 3424 may be optionally included (zero, one or more may be included) to allow for water removal after cleaning the vent 3400. The openings 3424 may allow water to be shaken out of the vent 3400 and/or allow greater opportunity for water to evaporate and exit the vent 3400, where both shaking and evaporation contribute to drying the vent 3400. If the openings 3424 are included, they are preferably located and sized so that, in conjunction with the diffusing material 3406, opening 3416 and gap 3412, substantially no air exits the openings 3424 when therapy pressure is applied to the patient interface 3000. In order to determine flow out of the openings 3424, pressure may be applied to the patient interface 3000 and the flow rate through the vent 3400 is measured. Then, the openings 3424 may be completely blocked and the flow rate re-measured. If the flow rate decreases by less than a predetermined percentage, then there is substantially no decrease in air flow through the vent 3400. Preferably, the flow rate decreases by no more than 5%, and more preferably the flow rate decreases by no more than 3%. In fact, blocking the openings 3424 may cause no change in the flow rate through the vent 3400. By designing the vent 3400 so that completely blocking the openings 3424 results in substantially no change in flow through the vent 3400, the vent 3400 should provide sufficient gas-washout even if the diffusing material 3406 becomes completely clogged, which could occur due to water or mucous build-up.

The openings 3424 may be formed in an area adjacent the side of the diffusing material 3406 that is opposite to the side facing the openings 3420. However, the size and the location of the openings 3424 can vary. The openings 3424 may have at least two purposes—to allow the vent to be washed and dried. First, the openings 3424 may allow the diffusing material 3406 to be washed by a user by way of placing the entire vent 3400 under water from a faucet. For washing to be effective, the openings 3424 are preferably sufficiently large to allow liquid water (e.g., droplets) to enter the housing. Second, the openings 3424 may allow, after a wash or after an inadvertent accumulation of liquid (e.g., mucous, water, etc.) during use of the vent, for the removal of the accumulated liquid. The size of each single opening 3424 is related to the ability to allow liquid such as water to move in and out of the event. The combined size of all of the openings may determine how efficiently the vent is washed and dried. A combined area of between 20 mm$^2$ and 80 mm$^2$ is believed to be able to allow adequate washing and drying. In some examples, the total opening areas is preferably between 30 and 60 mm$^2$, and even more preferably around 50 mm$^2$. The location of the openings may also be significant. It is preferable that openings 3424 are spaced from and located, at least to an extent, opposite to the openings 3416 with respect to the diffusing material 3406. This provides a water or liquid flow path between openings 3416 and 3424, which improves the ability to clean and dry the diffusing material 3406. With at least the embodiment illustrated in FIG. 4A, water may be removed at least through the second opening 3424 by shaking, or applying centripetal force to, the vent 3400.

The housing 3408 may hold the diffusing material 3406 is place by any suitable method. For example, the housing 3408 and diffusing material 3406 may be bonded together (e.g., glued or melted together) or mechanically fastened (e.g., friction, interference, detent, etc.).

The housing 3408 may be a single integral piece or multiple pieces or multiple pieces joined together into a single piece. The wall 3404 may be permanently joined to, or integrally formed with, the housing 3408. The housing may be attached to the vent 3400 in a non-releasable manner, which is attachment that is not intended to be detached without breaking. Non-releasable attachment may include glue, ultrasonic welding, melting with a hot iron, one-time snap fit (e.g., snap fit that is designed to break upon separation), originally formed as one piece, etc. If the housing 3408 is formed such that the housing 3408 and/or the diffusing material 3406 cannot be removed, some benefits may be achieved. For example, if the housing 3408 and/or the diffusing material 3406 cannot be removed, incorrect user installation or inadvertent detachment of the vent can be avoided.

FIG. 4B illustrates another configuration of the vent 3400. The descriptions associated with the reference numbers of FIG. 4A are also applicable here, and thus not repeated. This configuration of the vent 3400 is similar to that illustrated in FIG. 4A except that the air passage 3410 is omitted. Thus the gap 3412 extends from one side of the vent 3400 to the other.

FIG. 4C illustrates another configuration of the vent 3400. The descriptions associated with the reference numbers of FIG. 4A are also applicable here, and thus not repeated. Here, the air passage 3410 is omitted and instead a member 3426 is illustrated, which may secure the diffusing material 3406 and/or housing 3408.

FIG. 4D illustrates another configuration of the vent 3400. The descriptions associated with the reference numbers of FIG. 4A are also applicable here, and thus not repeated. This figure differs from FIG. 4A in that the locations of the openings 3424 are different. This figure also illustrates that the opening 3416 may be a continuous opening all around a periphery of the vent 3400. The openings 3424 may also be continuous, however are preferably discontinuous from each other and/or from the opening 3416.

FIG. 4E illustrates another configuration of the vent 3400. The descriptions associated with the reference numbers of FIG. 4A are also applicable here, and thus not repeated. In this configuration, the passages 3402 are in communication with and arrayed around the air passage 3410, resulting in the vent 3400 having an overall annular configuration compared to the planar configuration of FIGS. 4A-4D. In other words, the passages 3402 in FIGS. 4A-4D are in one planar or near-planar wall 3404, whereas the wall 3404 in FIG. 4E is cylindrical and the gas exiting the vent 3400 exits along the cylinder axis indicated with an interrupted line.

FIG. 4F illustrates another configuration of the vent 3400. The descriptions associated with the reference numbers of FIG. 4A are also applicable here, and thus not repeated. FIG. 4F is similar to FIG. 4E except that opening 3416 is provided at two ends of the diffusing material 3406 in FIG. 4F, but only at one end in FIG. 4E.

In each of FIGS. 4A-4F, the arrows illustrated through the diffusing material 3406 are conceptual illustrations of air flow through the diffusing material 3406 and may not be representative of actual air flow through the diffusing material 3406. In general, each of these arrows shows the concept of air exiting the passages 3402, entering the diffusing material 3406 via the surface 3414, exiting the diffusing material via the surface 3414, flowing through the gap 3412 and then to ambient via the opening 3416.

FIGS. 4G-4I illustrate another configuration of the vent 3400. The descriptions associated with the reference numbers of FIG. 4A are also applicable here, and thus not repeated except as noted. FIG. 4G illustrates an example of the vent 3400 in a perspective view, where the vent 3400 is an insertable and/or removable assembly. FIG. 4H is a top view where a top cover 3440 has been omitted so that the interior structure is visible. FIG. 4I is a cross-sectional view of FIG. 4H, but with the top cover included. This configuration of the vent 3400 is similar to that illustrated in FIG. 4B in that the air passage 3410 is omitted (but could be included if desired). As best seen in FIG. 4I, a support 3434 contacts the surface 3414 to support the diffusing material 3406. As illustrated in FIGS. 4H and 4I, the support 3434 is illustrated as a contiguous wall that bisects the gap 3412, extending uninterrupted from one side to another. However, the support 3434 need not be contiguous and could be a formed by one or more non-contiguous supports (one or more gaps could be provided in the support 3434).

Another difference is the position of the openings 3416. Instead of being substantially in line with the gap 3412, the openings 3416 are offset in a direction away from the surface that includes openings 3420, resulting in a second portion 3412A of the gap 3412 around a periphery of the diffusing material 3406. With this arrangement, the air can flow into the surface 3414 and out of a lateral surface 3436 of the diffusing material 3406 before flowing out through the openings 3416. The air can also flow through the gap 3412 and the second portion 3412A without passing through the diffusing material 3406. With the chaotic and unpredictable nature of the flow of individual molecules, the actual air flow may be a combination of both flow paths. However, by providing both flow paths, the vent 3400 may provide adequate flow even if the diffusing material 3406 becomes clogged.

FIGS. 4G and 4I illustrate a groove 3438 around a perimeter of the vent 3400. Such a groove may allow for the vent 3400 to be retained in a mating hole, preferably in a replaceable manner. If, for example, the hole is made in a relatively flexible material such as silicone, the vent 3400 may be readily removed so that actions such as cleaning or replacement can be performed in a simple manner.

FIGS. 4J and 4K illustrate aspects similar to FIG. 4I but with the addition of a deflector 3442. In FIG. 4J, the deflector 3442 is illustrated as a solid, flat obstruction that prevents air flowing straight through the diffusing material 3406 to the wall 3428 (e.g., out an opposite side from the surface 3414). In FIG. 4K, the deflector 3442 is curved in a manner that may generate a more smooth transition out of the sides of the diffusing material 3406 than the flat deflector illustrated in FIG. 4J. Although multiple pieces of the deflector 3442 are illustrated in FIG. 4K, any number of pieces, including a single piece, may be utilized as necessary for achieving desired flow characteristics. For both versions of the deflector 3442, any suitable method for producing the deflector 3442 within the diffusing material 3406 may be used. For example, an appropriately shaped cut in the side of the diffusing material 3406 may allow for insertion of the deflector 3442. Alternatively, the diffusing material 3406 may be made from multiple pieces that are then joined around the diffusing material 3406.

In one aspect, the diffusing material 3406 may be removable. For example, if the cover 3440 is attached in a releasable manner, the diffusing material 3406 may be retained through mechanical retention by way of the cover 3440. If the cover 3440 is removed, the diffusing material 3406 could also be removed. However, the diffusing material 3406 may not be removable in another aspect. For example, if the cover 3440 is attached to the vent 3400 such that the cover can only be removed by damage to the vent 3400, the diffusing material 3406 may be considered not removable. Alternatively, the diffusing material 3406 could be attached within the vent 3400 in a permanent manner, such as by adhesive, so that the diffusing material 3406 would be damaged during removal. Even if the cover 3440 is removable without causing damage, the diffusing material 3406 could be fixed in a manner that would damage or destroy the diffusing material 3406, thus making the diffusing material 3406 not removable.

Although a boundary of the diffusing material 3406 is described as a surface 3414, it may be different from a surface as of a solid body. The diffusing material 3406 may have many openings or gaps to allow tortious flow through the diffusing material. Thus the surface 3414 may also be considered a boundary of the diffusing material 3406.

The vent 3400 may produce relatively low volume of noise or suppress noise generated before the sound waves propagate to a user. Preferably, the sound generated is less than 28 dB(A). For example, the sound may be 20-28 dB(A), 22-26 dB(A), or about 24 dB(A). These sound levels may be sufficiently low that neither the user nor a bed partner is disturbed.

4.3.5 Decoupling Structure(s)

In one form the patient interface 3000 includes at least one decoupling structure, for example, a swivel or a ball and socket.

4.3.6 Connection Port

Connection port 3600 allows for connection to the air circuit 4170.

4.3.7 Forehead Support

In one form, the patient interface 3000 includes a forehead support 3700.

4.3.8 Anti-Asphyxia Valve

In one form, the patient interface 3000 includes an anti-asphyxia valve.

4.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

4.4 GLOSSARY

For the purposes of the present technology disclosure, in certain forms of the present technology, one or more of the following definitions may apply. In other forms of the present technology, alternative definitions may apply.

4.4.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

4.4.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

4.4.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

4.4.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

4.4.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

4.4.4 Anatomy
4.4.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

4.4.4.2 Anatomy of the Skull

Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

4.4.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

4.4.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

4.4.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

4.4.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

4.4.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical-topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

4.4.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

4.4.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

4.5 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

4.6 REFERENCE SIGNS LIST

1000 patient
1100 bed partner
3000 patient interface
3100 seal-forming structure
3200 plenum chamber
3300 structure
3400 vent
3402 passage
3404 wall
3406 diffusing material
3408 housing
3410 air passage
3412 gap
3412A second portion
3414 surface
3416 opening
3418 portion
3420 opening
3422 arrow
3424 opening
3426 member
3428 wall
3430 center line
3432 center line
3434 support
3436 lateral surface
3438 groove
3440 cover
3442 deflector
3600 connection port
3700 forehead support
4000 RPT device
4170 air circuit
5000 humidifier

The invention claimed is:

1. A gas washout vent for a patient interface system configured to maintain a therapy pressure in a range of about 4 cmH$_2$O to about 30 cmH$_2$O above ambient air pressure in use, throughout a patient's respiratory cycle, while the patient is sleeping, to ameliorate a respiratory or a sleep disordered breathing condition, the gas washout vent comprising:

a housing comprising a first wall with one or more passages through the first wall, the one or more passages being configured to provide fluid communication with a portion of the patient interface system that is configured to be exposed to the therapy pressure, the one or more passages each including a respective first opening on a first surface of the first wall, the housing at least partially defining a second opening that is in communication with ambient atmosphere; and a diffusing material located at least partially within the housing to be adjacent the first surface, wherein the diffusing material is spaced away from the housing by a gap that extends to provide fluid communication between all of the first openings, as well as between all of the first openings and the second opening, wherein the housing is configured so that air is prevented from flowing out of the housing at all areas directly opposite each of the first openings, wherein the second opening is spaced away from the first surface in a direction perpendicular to the first surface, wherein the diffusing material and a material of the first wall are different materials, wherein a surface of the diffusing material facing the first surface is spaced away from the first surface by a first portion of the gap, wherein a lateral surface of the diffusing material facing the second opening is spaced away from the second opening by a second portion of the gap, and wherein the diffusing material is configured and arranged such that air flows along a first flow path into the surface of the diffusing material facing the first surface, through the diffusing material, and out of the lateral surface of the diffusing material before flowing out through the second opening, and a second flow path through the first and second portions of the gap without passing through the diffusing material.

2. The gas washout vent according to claim 1, wherein the lateral surface of the diffusing material is transverse to the surface of the diffusing material facing the first surface.

3. The gas washout vent according to claim 1, wherein the first portion of the gap is immediately adjacent to the surface of the diffusing material facing the first surface and the second portion of the gap is immediately adjacent to the lateral surface of the diffusing material.

4. The gas washout vent according to claim 1, further comprising a deflector arranged within a thickness of the diffusing material, is the deflector configured to prevent air that enters the surface of the diffusing material facing the first surface from flowing directly through the thickness of the diffusing material and out an opposite side of the diffusing material.

5. A system for treating a respiratory disorder in a patient, comprising:
a respiratory pressure therapy device;
a humidifier;
an air circuit; and
a patient interface,
wherein at least one of the air circuit and the patient interface comprises the gas washout vent according to claim 1.

6. The gas washout vent according to claim 4, wherein the deflector is configured and arranged such that at least a portion of the air that flows into the thickness of the diffusing material is directed out of the lateral surface of the diffusing material by the deflector.

7. The gas washout vent according to claim 4, wherein the deflector comprises a solid, flat obstruction within the diffusing material.

8. The gas washout vent according to claim 4, wherein the deflector comprises a solid, curved obstruction within the diffusing material.

9. The gas washout vent according to claim 1, further comprising a support contacting the surface of the diffusing material facing the first surface to support the diffusing material.

10. The gas washout vent according to claim 1, wherein the surface of the diffusing material facing the first surface and the first surface are parallel.

11. The gas washout vent according to claim 1, wherein a portion of the housing is removable to allow replacement of the diffusing material.

\* \* \* \* \*